US010675357B2

(12) United States Patent
Lopez et al.

(10) Patent No.: US 10,675,357 B2
(45) Date of Patent: Jun. 9, 2020

(54) ANTIBODIES HAVING SPECIFICITY TO NECTIN-4 AND USES THEREOF

(71) Applicants: INSERM (INSTITUT NATIONAL DE LA SANTÉ ET DE LA RECHERCHE MÉDICALE), Paris (FR); UNIVERSITÉ D'AIX MARSEILLE, Marseilles (FR); CENTRE NATIONAL DE LA RECHERCHE SCIENTIFIQUE (CNRS), Paris (FR); INSTITUT JEAN PAOLI & IRENE CALMETTES, Marseilles (FR)

(72) Inventors: Marc Lopez, Marseilles (FR); Daniel Olive, Marseilles (FR)

(73) Assignees: INSERM (INSTITUT NATIONAL DE LA SANTÉ ET DE LA RECHERCHE MÉDICALE, Paris (FR); UNIVERSITÉ D'AIX MARSEILLE, Marseilles (FR); CENTRE NATIONAL DE LA RECHERCHE SCIENTIFIQUE (CNRS), Paris (FR); INSTITUT JEAN PAOLI & IRENE CALMETTES, Marseilles (FR)

( * ) Notice: Subject to any disclaimer, the term of this patent is extended or adjusted under 35 U.S.C. 154(b) by 177 days.

(21) Appl. No.: 15/754,047

(22) PCT Filed: Sep. 7, 2016

(86) PCT No.: PCT/EP2016/071076
§ 371 (c)(1),
(2) Date: Feb. 21, 2018

(87) PCT Pub. No.: WO2017/042210
PCT Pub. Date: Mar. 16, 2017

(65) Prior Publication Data
US 2018/0243434 A1    Aug. 30, 2018

(30) Foreign Application Priority Data
Sep. 9, 2015    (EP) .................................. 15306370

(51) Int. Cl.
| A61K 39/395 | (2006.01) |
| A61K 47/68 | (2017.01) |
| C07K 16/28 | (2006.01) |
| A61K 47/66 | (2017.01) |
| A61K 45/06 | (2006.01) |
| A61K 38/00 | (2006.01) |
| A61P 35/00 | (2006.01) |
| A61K 38/17 | (2006.01) |

(52) U.S. Cl.
CPC ........ *A61K 47/6801* (2017.08); *A61K 39/395* (2013.01); *A61K 45/06* (2013.01); *A61K 47/67* (2017.08); *A61K 47/6899* (2017.08); *C07K 16/2803* (2013.01); *A61K 38/00* (2013.01); *A61K 38/177* (2013.01); *A61P 35/00* (2018.01); *C07K 2317/565* (2013.01); *C07K 2317/732* (2013.01); *C07K 2317/734* (2013.01)

(58) Field of Classification Search
CPC .......................... A61K 47/6801; A61K 39/395
USPC ...................................... 424/181.1
See application file for complete search history.

(56) References Cited

FOREIGN PATENT DOCUMENTS

| WO | 2005/111076 A1 | 11/2005 |
| WO | 2010/067487 A1 | 6/2010 |
| WO | 2012/047724 A1 | 4/2012 |
| WO | 2012/098465 A1 | 7/2012 |
| WO | WO 2013/16489 A2 * | 1/2013 |

OTHER PUBLICATIONS

"A Study if the Safety and Pharmacokinetics of AGS-22M6E in Subjects With Malignant Solid Tumors That Express Nectin-4", ClinicalTrials.goc—Archive, Jun. 22, 2015, retrieved from the Internet: URL:https://clinicaltrials.gov/archive/NCT01409135/2015_06_10.
Pavlova Natalya N et al: "A role for PVRL4-driven cell-cell interactions in tumorigenesis.", ELIFE, vol. 2, E00358, Apr. 30, 2013, pp. 1-24.
M. Mateo et al: "Different Roles of the Three Loops Forming the Adhesive Interface of Nectin-4 in Measles Virus Binding and Cell Entry, Nectin-4 Homodimerization, and Heretodimerization with Nectin-1", Journal of Virology., vol. 88, No. 24, Oct. 1, 2014, pp. 14161-14171.
R Lattanzio et al: "Membranous Nectin-4 expression is a risk factor for distant relapse of T1-T2, No luminal-A early breast cancer", Oncogenesis, vol. 3, No. 9, E118, Sep. 1, 2014, pp. 1-7.
Atsushi Takano et al: "Identification of Nectin-4 Oncoprotein as a Diagnostic and Therapeutic Target for Lung Cancer", Cacer Research, American Association for Cancer Research, US, vol. 69, No. 16, Aug. 15, 2009, pp. 6694-6703.

* cited by examiner

*Primary Examiner* — Sean E Aeder
(74) *Attorney, Agent, or Firm* — W&C IP

(57) ABSTRACT

The present invention relates to antibodies having specificity to nectin-4 and uses thereof.

14 Claims, 9 Drawing Sheets

Figure 1A:
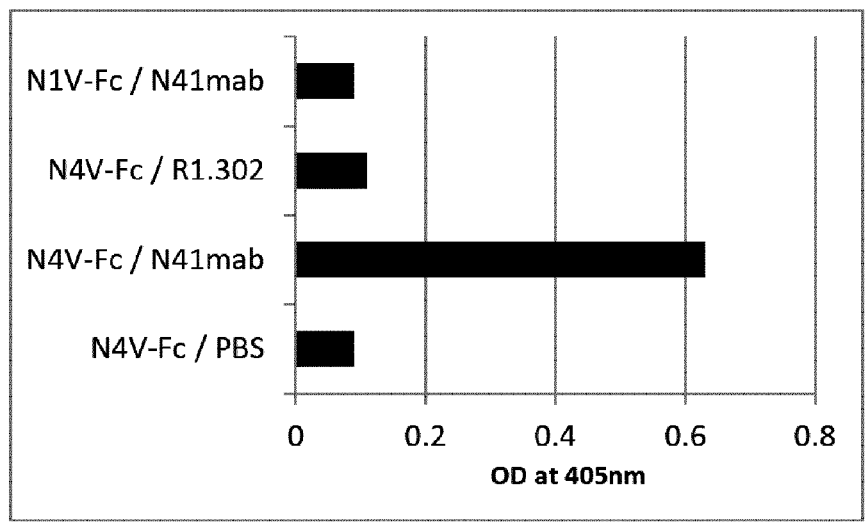

Specification includes a Sequence Listing.

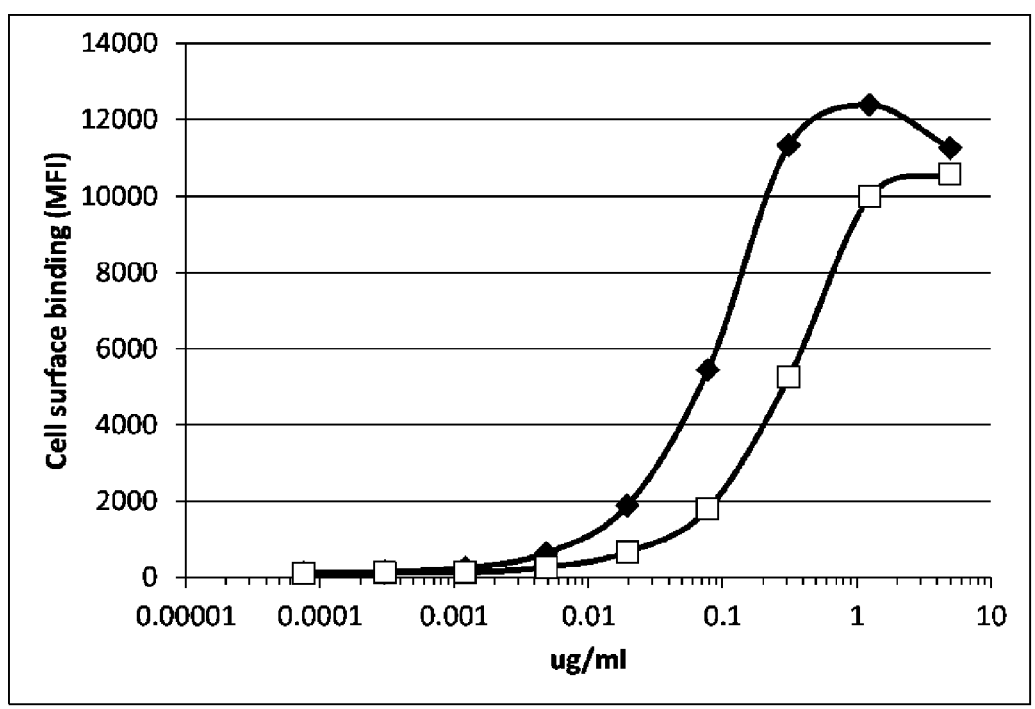
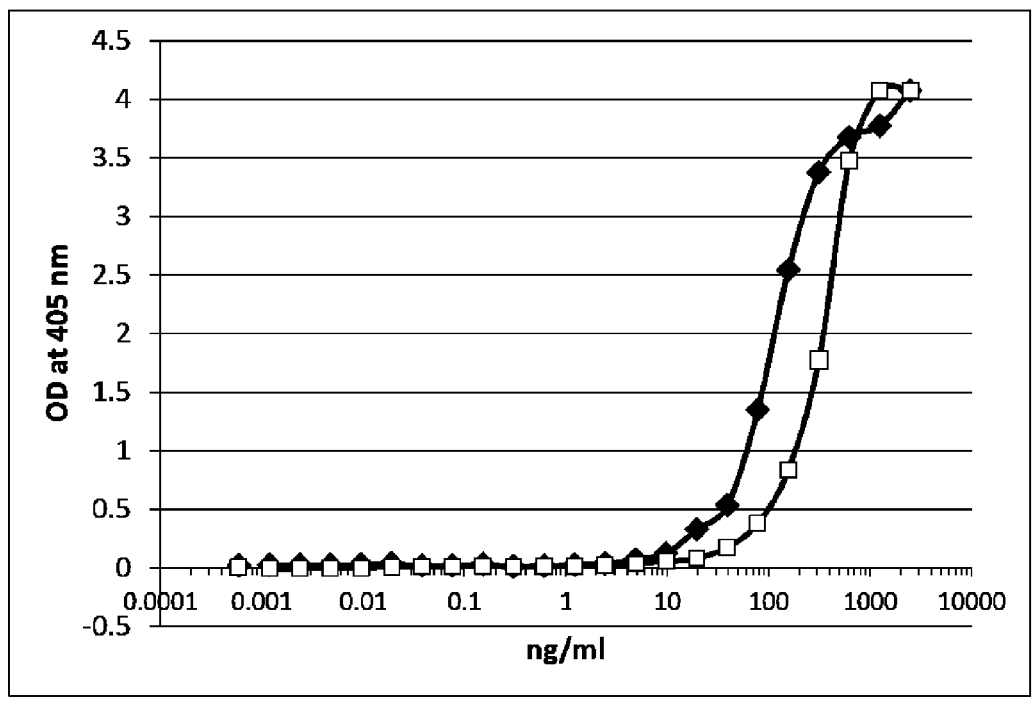
|  | EC50 FACS ug/ml | EC50 ELISA ug/ml |
|---|---|---|
| N41mab | 0.076 | 0.114 |
| Ha22-2 | 0.31 | 0.339 |
Figure 5 A and B A
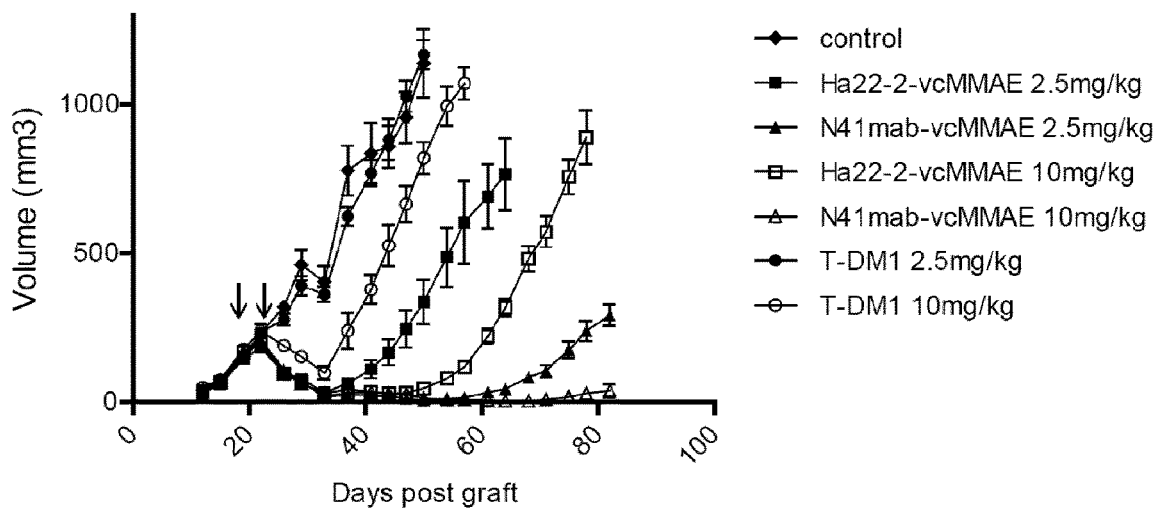
B
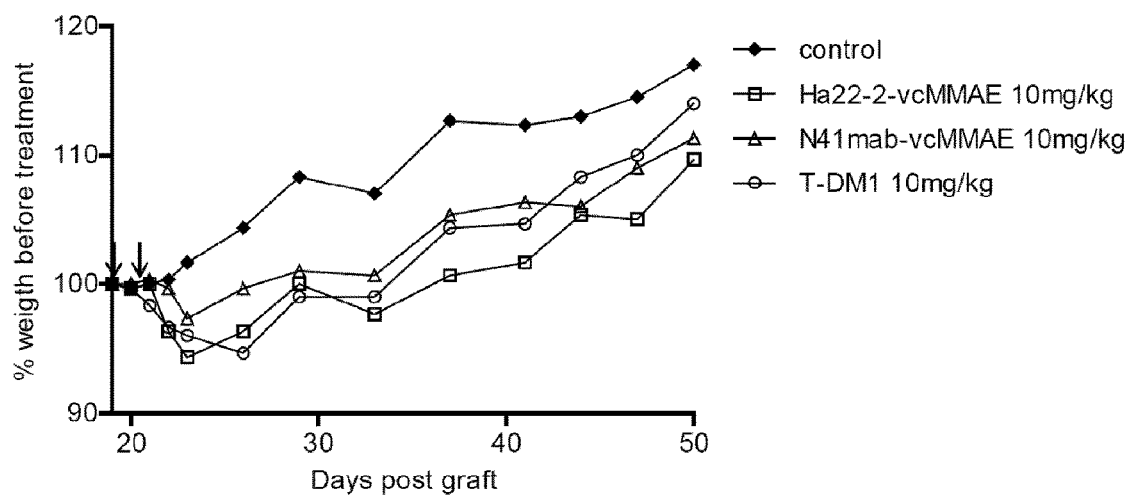
C
|  | Day |
|---|---|
| control | 27.5 |
| T-DM1 2.5mg/kg | 27.5 |
| Ha22-2-vcMMAE 2.5mg/kg | 50 |
| N41mab-vcMMAE 2.5mg/kg | 82 |
| T-DM1 10mg/kg | 42.5 |
| Ha22-2-vcMMAE 10mg/kg | 68 |
| N41mab-vcMMAE 10mg/kg | >82 |
Figure 8

SEQUENCE LISTING

```
<160> NUMBER OF SEQ ID NOS: 4

<210> SEQ ID NO 1
<211> LENGTH: 116
<212> TYPE: PRT
<213> ORGANISM: Artificial Sequence
<220> FEATURE:
<223> OTHER INFORMATION: Synthetic VH sequence

<400> SEQUENCE: 1

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Ser Thr Asp Tyr Asn Ala Ala Phe Ile
    50                  55                  60

Ser Arg Leu Ser Ile Ser Lys Asp Thr Ser Lys Ser Gln Val Phe Phe
65                  70                  75                  80

Lys Met Asn Ser Leu Gln Ala Asp Asp Thr Ala Ile Tyr Tyr Cys Ala
                85                  90                  95

Arg Glu Leu Ile His Ala Met Asp Asn Trp Gly Gln Gly Thr Ser Val
            100                 105                 110

Thr Val Ser Ser
        115

<210> SEQ ID NO 2
<211> LENGTH: 106
<212> TYPE: PRT
<213> ORGANISM: Artificial Sequence
<220> FEATURE:
<223> OTHER INFORMATION: Synthetic VL sequence
```

<400> SEQUENCE: 2

Asp Ile Gln Met Thr Gln Ser Pro Ala Ser Leu Ser Val Val Gly
1               5                   10                  15

Glu Thr Val Thr Ile Thr Cys Arg Ala Ser Glu Asn Ile Tyr Ser Asn
            20                  25                  30

Leu Ala Trp Tyr Gln Gln Lys Gln Gly Asn Ser Pro Gln Leu Leu Val
        35                  40                  45

Phe Ala Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Thr Tyr Tyr Cys Gln His Phe Trp Gly Thr Pro Thr
                85                  90                  95

Phe Gly Gly Gly Thr Lys Leu Glu Ile Lys
            100                 105

<210> SEQ ID NO 3
<211> LENGTH: 348
<212> TYPE: DNA
<213> ORGANISM: Artificial Sequence
<220> FEATURE:
<223> OTHER INFORMATION: Synthetic Heavy chain DNA sequence

<400> SEQUENCE: 3
caggtgcagc tgaagcagtc aggacctggc ctagtgcagc cctcacagag cctgtccatc      60
acctgcacag tctctggttt ctcacttact aactatggtg tacactgggt tcgccagtct     120
ccaggaaagg gtctggagtg gctgggagtg atatggagtg gtggtagcac agactataat     180
gcagctttca tatccagact gagcatcagc aaggacacct ccaagagcca gttttctttt     240
aaaatgaaca gtctgcaagc tgatgacaca gccatatact actgtgccag agagttaatc     300
catgctatgg acaactgggg ccaaggaacc tcagtcaccg tctcctca                  348

<210> SEQ ID NO 4
<211> LENGTH: 318
<212> TYPE: DNA
<213> ORGANISM: Artificial Sequence
<220> FEATURE:
<223> OTHER INFORMATION: Synthetic Light chain DNA sequence

<400> SEQUENCE: 4
gacatccaga tgactcagtc tccagcctcc ctatctgtat ctgtgggaga aactgtcacc      60
atcacatgtc gagcaagtga gaatatttac agtaatttag catggtatca gcagaaacag     120
ggaaactctc ctcagctcct ggtctttgct gcaacaaact agcagatgg tgtgccatca      180 aggttcagtg gcagtggatc aggcacacag tattccctca agatcaacag cctgcagtct     240
gaagattttg ggacttatta ctgtcaacat ttttggggta ctccgacgtt cggtggaggc     300
accaagctgg aaatcaaa                                                   318

ANTIBODIES HAVING SPECIFICITY TO NECTIN-4 AND USES THEREOF

FIELD OF THE INVENTION

The present invention relates to antibodies having specificity to nectin-4 and uses thereof.

BACKGROUND OF THE INVENTION

Nectin-4 is a surface molecule that belongs to the nectin family of proteins, which comprises 4 members. Nectins are cell adhesion molecules that play a key role in various biological processes such as polarity, proliferation, differentiation and migration, for epithelial, endothelial, immune and neuronal cells, during development and adult life. They are involved in several pathological processes in humans. They are the main receptors for poliovirus, herpes simplex virus and measles virus. Mutations in the genes encoding Nectin-1 (PVRL1) or Nectin-4 (PVRL4) cause ectodermal dysplasia syndromes associated with other abnormalities. Nectin-4 is expressed during fetal development. In adult tissues its expression is more restricted than that of other members of the family. Nectin-4 is a tumor-associated antigen in 50%, 49% and 86% of breast, ovarian and lung carcinomas, respectively, mostly on tumors of bad prognosis. Its expression is not detected in the corresponding normal tissues. In breast tumors, Nectin-4 is expressed mainly in triple-negative and ERBB2$^+$ carcinomas. In the serum of patients with these cancers, the detection of soluble forms of Nectin-4 is associated with a poor prognosis. Levels of serum Nectin-4 increase during metastatic progression and decrease after treatment. These results suggest that Nectin-4 could a reliable target for the treatment of cancer. Accordingly, several anti-Nectin-4 antibodies have been described in the prior art. In particular, Enfortumab Vedotin (ASG-22ME) is an antibody-drug conjugate (ADC) targeting Nectin-4 and is currently clinically investigated for the treatment of patients suffering from solid tumors.

SUMMARY OF THE INVENTION

The present invention relates to antibodies having specificity to nectin-4 and uses thereof. In particular, the present invention is defined by the claims.

DETAILED DESCRIPTION OF THE INVENTION

The present invention relates to antibodies having specificity to Nectin-4 and uses thereof. In particular, the present invention provides antibodies that derive from the N41mab antibody (N41mab). The inventors indeed show that the N41mab had an intrinsic anti-metastatic activity: N41mab markedly reduced tumor invasive properties of nectin4 expressing breast tumor cells by reducing Matrigel invasion. Using xenografted mice models, they showed that treatment of mice with 10 mg/kg N41mab twice a week leads to a marked inhibition of tumor spread from primary site and also to a blockade of metastasis formation after systemic injection of tumor cells in mouse tail vein. Conjugation of the N41mab with auristatin-E (N41mab-MMAE) induced a marked inhibition of breast tumor cell growth in vitro, with an IC50 value of 5 ng/ml (33 pM). Mice treated at tumor onset with two injections i.v. of N41mab-MMAE at 2.5 or 10 mg/kg, induced a rapid and long-lasting tumor regression. More particularly, the inventors demonstrate that the N41mab is more efficient than the most advanced anti-nectin4 antibody described in the prior art (i.e. ASG-22ME). Accordingly the antibody thus represents a new way to treat cancer patients to prevent and/or eradicate tumor progression.

As used herein, the term "Nectin-4 has its general meaning in the art and includes human Nectin-4, in particular the native-sequence polypeptide, isoforms, chimeric polypeptides, all homologs, fragments, and precursors of human Nectin-4. The amino acid sequence for native Nectin-4 includes the NCBI Reference Sequence: NP 112178.2.

As used herein the term "antibody" or "immunoglobulin" have the same meaning, and will be used equally in the present invention. The term "antibody" as used herein refers to immunoglobulin molecules and immunologically active portions of immunoglobulin molecules, i.e., molecules that contain an antigen binding site that immunospecifically binds an antigen. As such, the term antibody encompasses not only whole antibody molecules, but also antibody fragments as well as variants (including derivatives) of antibodies and antibody fragments. In natural antibodies, two heavy chains are linked to each other by disulfide bonds and each heavy chain is linked to a light chain by a disulfide bond. There are two types of light chain, lambda (l) and kappa (κ). There are five main heavy chain classes (or isotypes) which determine the functional activity of an antibody molecule: IgM, IgD, IgG, IgA and IgE. Each chain contains distinct sequence domains. The light chain includes two domains, a variable domain (VL) and a constant domain (CL). The heavy chain includes four domains, a variable domain (VH) and three constant domains (CHI, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, trans-placental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from nonhypervariable or framework regions (FR) can participate to the antibody binding site or influence the overall domain structure and hence the combining site. Complementarity Determining Regions or CDRs refer to amino acid sequences which together define the binding affinity and specificity of the natural Fv region of a native immunoglobulin binding site. The light and heavy chains of an immunoglobulin each have three CDRs, designated L-CDR1, L-CDR2, L-CDR3 and H-CDR1, H-CDR2, H-CDR3, respectively. An antigen-binding site, therefore, typically includes six CDRs, comprising the CDR set from each of a heavy and a light chain V region. Framework Regions (FRs) refer to amino acid sequences interposed between CDRs. The residues in antibody variable domains are conventionally numbered according to a system devised by Kabat et al. This system is set forth in Kabat et al., 1987, in Sequences of Proteins of Immunological Interest, US Department of Health and Human Services, NIH, USA (hereafter "Kabat et al."). This numbering system is used in the present specification. The Kabat residue designations do not always correspond directly with the linear numbering of the amino acid residues in SEQ ID sequences. The actual linear amino acid sequence may contain fewer or additional amino acids than in the strict Kabat numbering corresponding to a shortening of, or insertion into, a structural component, whether framework or complementarity determining region (CDR), of the basic variable domain structure. The correct Kabat numbering of residues may be determined for a given antibody by alignment of residues of homology in the sequence of the antibody with a "standard" Kabat numbered sequence. The CDRs of the heavy chain variable domain are located at residues 31-35B (H-CDR1), residues 50-65 (H-CDR2) and residues 95-102 (H-CDR3) according to the Kabat numbering system. The CDRs of the light chain variable domain are located at residues 24-34 (L-CDR1), residues 50-56 (L-CDR2) and residues 89-97 (L-CDR3) according to the Kabat numbering system.

As used herein, the term "specificity" refers to the ability of an antibody to detectably bind an epitope presented on an antigen, such as a Nectin-4, while having relatively little detectable reactivity with non-Nectin-4 proteins or structures (such as other proteins presented on NK cells, or on other cell types). Specificity can be relatively determined by binding or competitive binding assays, using, e.g., Biacore instruments, as described elsewhere herein. Specificity can be exhibited by, e.g., an about 10:1, about 20:1, about 50:1, about 100:1, 10.000:1 or greater ratio of affinity/avidity in binding to the specific antigen versus nonspecific binding to other irrelevant molecules (in this case the specific antigen is a Nectin-4 polypeptide). The term "affinity", as used herein, means the strength of the binding of an antibody to an epitope. The affinity of an antibody is given by the dissociation constant Kd, defined as [Ab]×[Ag]/[Ab–Ag], where [Ab–Ag] is the molar concentration of the antibody-antigen complex, [Ab] is the molar concentration of the unbound antibody and [Ag] is the molar concentration of the unbound antigen. The affinity constant Ka is defined by 1/Kd. Preferred methods for determining the affinity of mAbs can be found in Harlow, et al., Antibodies: A Laboratory Manual, Cold Spring Harbor Laboratory Press, Cold Spring Harbor, N.Y., 1988), Coligan et al., eds., Current Protocols in Immunology, Greene Publishing Assoc. and Wiley Interscience, N.Y., (1992, 1993), and Muller, Meth. Enzymol. 92:589-601 (1983), which references are entirely incorporated herein by reference. One preferred and standard method well known in the art for determining the affinity of mAbs is the use of Biacore instruments.

According to the present invention, the VH region of the N41mab consists of the sequence of SEQ ID NO:1. Accordingly, the H-CDR1 of N41mab is defined by the sequence ranging from the amino acid residue at position 31 to the amino acid residue at position 35 in SEQ ID NO:1. Accordingly, the H-CDR2 of N41mab is defined by the sequence ranging from the amino acid residue at position 50 to the amino acid residue at position 65 in SEQ ID NO:1. Accordingly, the H-CDR3 of N41mab is defined by the sequence ranging from the amino acid residue at position 98 to the amino acid residue at position 105 in SEQ ID NO:1.

```
SEQ ID NO: 1: VH region of N41mab FR1-CDR1-FR2-
CDR2-FR3-CDR3-FR4
QVQLKQSGPGLVQPSQSLSITCTVSGFSLTNYGVHWVRQSPGKGLEWLG

VIWSGGSTDYNAAFISRLSISKDTSKSQVFFKMNSLQADDTAIYYCARE

LIHAMDNWGQGTSVTVSS
```

According to the present invention, the VL region of the N41mab antibody consists of the sequence of SEQ ID NO:2. Accordingly, the L-CDR1 of N41mab is defined by the sequence ranging from the amino acid residue at position 24 to the amino acid residue at position 34 in SEQ ID NO:2. Accordingly, the L-CDR2 of N41mab is defined by the sequence ranging from the amino acid residue at position 50 to the amino acid residue at position 56 in SEQ ID NO:2. Accordingly, the L-CDR3 of N41mab is defined by the sequence ranging from the amino acid residue at position 89 to the amino acid residue at position 96 in SEQ ID NO:2.

SEQ ID NO:2: VL region of N41mab antibody FR1-CDR1-FR2-CDR2-FR3-CDR3-FR4

```
DIQMTQSPASLSVSVGETVTITCRASENIYSNLAWYQQKQGNSPQLLVF

AATNLADGVPSRFSGSGSGTQYSLKINSLQSEDFGTYYCQHFWGTPTFG

GGTKLEIK
```

The present invention thus provides antibodies comprising functional variants of the VL region, VH region, or one or more CDRs of N41mab. A functional variant of a VL, VH, or CDR used in the context of a monoclonal antibody of the present invention still allows the antibody to retain at least a substantial proportion (at least about 50%, 60%, 70%, 80%, 90%, 95% or more) of the affinity/avidity and/or the specificity/selectivity of the parent antibody (i.e. N41mab antibody) and in some cases such a monoclonal antibody of the present invention may be associated with greater affinity, selectivity and/or specificity than the parent Ab. Such functional variants typically retain significant sequence identity to the parent Ab. The sequence of CDR variants may differ from the sequence of the CDR of the parent antibody sequences through mostly conservative substitutions; for instance at least about 35%, about 50% or more, about 60% or more, about 70% or more, about 75% or more, about 80% or more, about 85% or more, about 90% or more, (e.g., about 65-95%, such as about 92%, 93% or 94%) of the substitutions in the variant are conservative amino acid residue replacements. The sequences of CDR variants may differ from the sequence of the CDRs of the parent antibody sequences through mostly conservative substitutions; for instance at least 10, such as at least 9, 8, 7, 6, 5, 4, 3, 2 or 1 of the substitutions in the variant are conservative amino acid residue replacements. In the context of the present invention, conservative substitutions may be defined by substitutions within the classes of amino acids reflected as follows:

Aliphatic residues I, L, V, and M
Cycloalkenyl-associated residues F, H, W, and Y
Hydrophobic residues A, C, F, G, H, I, L, M, R, T, V, W, and Y
Negatively charged residues D and E
Polar residues C, D, E, H, K, N, Q, R, S, and T
Positively charged residues H, K, and R
Small residues A, C, D, G, N, P, S, T, and V
Very small residues A, G, and S
Residues involved in turn A, C, D, E, G, H, K, N, Q, R, S, P, and formation T
Flexible residues Q, T, K, S, G, P, D, E, and R
More conservative substitutions groupings include: valine-leucine-isoleucine, phenylalanine-tyrosine, lysine-arginine, alanine-valine, and asparagine-glutamine. Conservation in terms of hydropathic/hydrophilic properties and residue weight/size also is substantially retained in a variant CDR as compared to a CDR of N41mab. The importance of the hydropathic amino acid index in conferring interactive biologic function on a protein is generally understood in the art. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophane (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). The retention of similar residues may also or alternatively be measured by a similarity score, as determined by use of a BLAST program (e.g., BLAST 2.2.8 available through the NCBI using standard settings BLOSUM62, Open Gap=11 and Extended Gap=1). Suitable variants typically exhibit at least about 70% of identity to the parent peptide. According to the present invention a first amino acid sequence having at least 70% of identity with a second amino acid sequence means that the first sequence has 70; 71; 72; 73; 74; 75; 76; 77; 78; 79; 80; 81; 82; 83; 84; 85; 86; 87; 88; 89; 90; 91; 92; 93; 94; 95; 96; 97; 98; 99; or 100% of identity with the second amino acid sequence. According to the present invention a first amino acid sequence having at least 90% of identity with a second amino acid sequence means that the first sequence has 90; 91; 92; 93; 94; 95; 96; 97; 98; 99; or 100% of identity with the second amino acid sequence.

In some embodiments, the antibody of the present invention is an antibody having a heavy chain comprising i) a H-CDR1 having at least 90% of identity with the H-CDR1 of N41mab, ii) a H-CDR2 having at least 90% of identity with the H-CDR2 of N41mab and iii) a H-CDR3 having at least 90% of identity with the H-CDR3 of N41mab.

In some embodiments, the antibody of the present invention is an antibody having a light chain comprising i) a L-CDR1 having at least 90% of identity with the L-CDR1 of N41mab, ii) a L-CDR2 having at least 90% of identity with the L-CDR2 of N41mab and iii) a L-CDR3 having at least 90% of identity with the L-CDR3 of N41mab.

In some embodiments, the antibody of the present invention is an antibody having a heavy chain comprising i) a H-CDR1 having at least 90% of identity with the H-CDR1 of N41mab, ii) a H-CDR2 having at least 90% of identity with the H-CDR2 of N41mab and iii) a H-CDR3 having at least 90% of identity with the H-CDR3 of N41mab and a light chain comprising i) a L-CDR1 having at least 90% of identity with the L-CDR1 of N41mab, ii) a L-CDR2 having at least 90% of identity with the L-CDR2 of N41mab and iii) a L-CDR3 having at least 90% of identity with the L-CDR3 of N41mab.

In some embodiments, the antibody of the present invention is an antibody having a heavy chain comprising i) the H-CDR1 of N41mab, ii) the H-CDR2 of N41mab and iii) the H-CDR3 of N41mab.

In some embodiments, the antibody of the present invention is an antibody having a light chain comprising i) the L-CDR1 of N41mab, ii) the L-CDR2 of N41mab and iii) the L-CDR3 of N41mab.

In some embodiments, the antibody of the present invention is an antibody having a heavy chain comprising i) the H-CDR1 of N41mab, ii) the H-CDR2 of N41mab and iii) the H-CDR3 of N41mab and a light chain comprising i) the L-CDR1 of N41mab, ii) the L-CDR2 of N41mab and iii) the L-CDR3 of N41mab.

In some embodiments, the antibody of the present invention is an antibody having a heavy chain having at least 70% of identity with SEQ ID NO:1

In some embodiments, the antibody of the present invention is an antibody having a light chain having at least 70 of identity with SEQ ID NO:2.

In some embodiments, the antibody of the present invention is an antibody having a heavy chain having at least 70% of identity with SEQ ID NO:1 and a light chain having at least 70% of identity with SEQ ID NO:2.

In some embodiments, the antibody of the present invention is an antibody having a heavy chain which is identical to SEQ ID NO:1

In some embodiments, the antibody of the present invention is an antibody having a light chain identical to SEQ ID NO:2.

In some embodiments, the antibody of the present invention is an antibody having a heavy chain identical to SEQ ID NO:1 and a light chain identical to SEQ ID NO:2.

In some embodiments, the antibody of the present invention is a chimeric antibody, typically a chimeric mouse/human antibody. The term "chimeric antibody" refers to a monoclonal antibody which comprises a VH domain and a VL domain of an antibody derived from a non-human animal, a CH domain and a CL domain of a human antibody. As the non-human animal, any animal such as mouse, rat, hamster, rabbit or the like can be used. In particular, said mouse/human chimeric antibody may comprise the heavy chain and the light chain of the N41mab antibody.

In some embodiments, the antibody of the present invention is a humanized antibody which comprises the CDRs of the N41mab antibody. As used herein the term "humanized antibody" refers to antibodies in which the framework or "complementarity determining regions" (CDR) have been modified to comprise the CDR from a donor immunoglobulin of different specificity as compared to that of the parent immunoglobulin.

In some embodiments, the antibody of the present invention is selected from the group of Fab, F(ab')2, Fab' and scFv. As used herein, the term "Fab" denotes an antibody fragment having a molecular weight of about 50,000 and antigen binding activity, in which about a half of the N-terminal side of H chain and the entire L chain, among fragments obtained by treating IgG with a protease, papaine, are bound together through a disulfide bond. The term "F(ab')2" refers to an antibody fragment having a molecular weight of about 100,000 and antigen binding activity, which is slightly larger than the Fab bound via a disulfide bond of the hinge region, among fragments obtained by treating IgG with a protease, pepsin. The term "Fab'" refers to an antibody fragment having a molecular weight of about 50,000 and antigen binding activity, which is obtained by cutting a disulfide bond of the hinge region of the F(ab')2. A single chain Fv ("scFv") polypeptide is a covalently linked VH::VL heterodimer which is usually expressed from a gene fusion including VH and VL encoding genes linked by a peptide-encoding linker. The human scFv fragment of the invention includes CDRs that are held in appropriate conformation, preferably by using gene recombination techniques.

In another aspect, the invention provides an antibody that competes for binding to Nectin-4 with the antibody of the invention.

As used herein, the term "binding" in the context of the binding of an antibody to a predetermined antigen or epitope typically is a binding with an affinity corresponding to a $K_D$ of about $10^{-7}$ M or less, such as about $10^{-8}$ M or less, such as about $10^{-9}$ M or less, about $10^{-10}$ M or less, or about $10^{-11}$ M or even less when determined by for instance surface plasmon resonance (SPR) technology in a BIAcore 3000 instrument using a soluble form of the antigen as the ligand and the antibody as the analyte. BIACORE® (GE Healthcare, Piscaataway, N.J.) is one of a variety of surface plasmon resonance assay formats that are routinely used to epitope bin panels of monoclonal antibodies. Typically, an antibody binds to the predetermined antigen with an affinity corresponding to a $K_D$ that is at least ten-fold lower, such as at least 100-fold lower, for instance at least 1,000-fold lower, such as at least 10,000-fold lower, for instance at least 100,000-fold lower than its $K_D$ for binding to a non-specific antigen (e.g., BSA, casein), which is not identical or closely related to the predetermined antigen. When the $K_D$ of the antibody is very low (that is, the antibody has a high affinity), then the $K_D$ with which it binds the antigen is typically at least 10,000-fold lower than its $K_D$ for a non-specific antigen. An antibody is said to essentially not bind an antigen or epitope if such binding is either not detectable (using, for example, plasmon resonance (SPR) technology in a BIAcore 3000 instrument using a soluble form of the antigen as the ligand and the antibody as the analyte), or is 100 fold, 500 fold, 1000 fold or more than 1000 fold less than the binding detected by that antibody and an antigen or epitope having a different chemical structure or amino acid sequence.

Additional antibodies can be identified based on their ability to cross-compete (e.g., to competitively inhibit the binding of, in a statistically significant manner) with other antibodies of the invention in standard Nectin-4 binding assays. The ability of a test antibody to inhibit the binding of antibodies of the present invention to Nectin-4 demonstrates that the test antibody can compete with that antibody for binding to Nectin-4 such an antibody may, according to non-limiting theory, bind to the same or a related (e.g., a structurally similar or spatially proximal) epitope on Nectin-4 as the antibody with which it competes. Thus, another aspect of the invention provides antibodies that bind to the same antigen as, and compete with, the antibodies disclosed herein. As used herein, an antibody "competes" for binding when the competing antibody inhibits Nectin-4 binding of an antibody or antigen biding fragment of the invention by more than 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 or 99% in the presence of an equimolar concentration of competing antibody.

In other embodiments the antibodies or antigen binding fragments of the invention bind to one or more epitopes of Nectin-4. In some embodiments, the epitopes to which the present antibodies or antigen binding fragments bind are linear epitopes. In other embodiments, the epitopes to which the present antibodies or antigen binding fragments bind are non-linear, conformational epitopes.

The antibodies of the invention may be assayed for specific binding by any method known in the art. Many different competitive binding assay format(s) can be used for epitope binning. The immunoassays which can be used include, but are not limited to, competitive assay systems using techniques such western blots, radioimmunoassays, ELISA, "sandwich" immunoassays, immunoprecipitation assays, precipitin assays, gel diffusion precipitin assays, immunoradiometric assays, fluorescent immunoassays, protein A immunoassays, and complement-fixation assays. Such assays are routine and well known in the art (see, e.g., Ausubel et al., eds, 1994 Current Protocols in Molecular Biology, Vol. 1, John Wiley & sons, Inc., New York).

The antibodies of the present invention are produced by any technique known in the art, such as, without limitation, any chemical, biological, genetic or enzymatic technique, either alone or in combination. Typically, knowing the amino acid sequence of the desired sequence, one skilled in the art can readily produce said antibodies, by standard techniques for production of polypeptides. For instance, they can be synthesized using well-known solid phase method, preferably using a commercially available peptide synthesis apparatus (such as that made by Applied Biosystems, Foster City, Calif.) and following the manufacturer's instructions. Alternatively, antibodies of the present invention can be synthesized by recombinant DNA techniques well-known in the art. For example, antibodies can be obtained as DNA expression products after incorporation of DNA sequences encoding the antibodies into expression vectors and introduction of such vectors into suitable eukaryotic or prokaryotic hosts that will express the desired antibodies, from which they can be later isolated using well-known techniques.

Accordingly, a further object of the invention relates to a nucleic acid molecule encoding an antibody according to the invention. More particularly the nucleic acid molecule encodes a heavy chain or a light chain of an antibody of the present invention. More particularly the nucleic acid molecule comprises a nucleic acid sequence having 70% of identity with SEQ ID NO:3 or SEQ ID NO:4.

Heavy chain: DNA sequence FR1-CDR1-FR2-CDR2-FR3-CDR3-FR4

SEQ ID NO: 3

CAGGTGCAGCTGAAGCAGTCAGGACCTGGCCTAGTGCAGCCCTCACAGAG

CCTGTCCATCACCTGCACAGTCTCTGGTTTCTCACTTACTAACTATGGTG

TACACTGGGTTCGCCAGTCTCCAGGAAAGGGTCTGGAGTGGCTGGGAGTG

ATATGGAGTGGTGGTAGCACAGACTATAATGCAGCTTTCATATCCAGACT

GAGCATCAGCAAGGACACCTCCAAGAGCCAAGTTTTCTTTAAAATGAACA

GTCTGCAAGCTGATGACACAGCCATATACTACTGTGCCAGAGAGTTAATC

CATGCTATGGACAACTGGGGCCAAGGAACCTCAGTCACCGTCTCCTCA

Light chain: DNA sequence FR1-CDR1-FR2-CDR2-FR3-CDR3-FR4

SEQ ID NO: 4

GACATCCAGATGACTCAGTCTCCAGCCTCCCTATCTGTATCTGTGGGAGA

AACTGTCACCATCACATGTCGAGCAAGTGAGAATATTTACAGTAATTTAG

CATGGTATCAGCAGAAACAGGGAAACTCTCCTCAGCTCCTGGTCTTTGCT

GCAACAAACTTAGCAGATGGTGTGCCATCAAGGTTCAGTGGCAGTGGATC

AGGCACACAGTATTCCCTCAAGATCAACAGCCTGCAGTCTGAAGATTTTG

GGACTTATTACTGTCAACATTTTTGGGGTACTCCGACGTTCGGTGGAGGC

ACCAAGCTGGAAATCAAA

Typically, said nucleic acid is a DNA or RNA molecule, which may be included in any suitable vector, such as a plasmid, cosmid, episome, artificial chromosome, phage or a viral vector. As used herein, the terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence. So, a further object of the invention relates to a vector comprising a nucleic acid of the invention. Such vectors may comprise regulatory elements, such as a promoter, enhancer, terminator and the like, to cause or direct expression of said antibody upon administration to a subject. Examples of promoters and enhancers used in the expression vector for animal cell include early promoter and enhancer of SV40, LTR promoter and enhancer of Moloney mouse leukemia virus, promoter and enhancer of immunoglobulin H chain and the like. ny expression vector for animal cell can be used, so long as a gene encoding the human antibody C region can be inserted and expressed. Examples of suitable vectors include pAGE107, pAGE103, pHSG274, pKCR, pSG1 beta d2-4 and the like. Other examples of plasmids include replicating plasmids comprising an origin of replication, or integrative plasmids, such as for instance pUC, pcDNA, pBR, and the like. Other examples of viral vector include adenoviral, retroviral, herpes virus and AAV vectors. Such recombinant viruses may be produced by techniques known in the art, such as by transfecting packaging cells or by transient transfection with helper plasmids or viruses. Typical examples of virus packaging cells include PA317 cells, PsiCRIP cells, GPenv+ cells, 293 cells, etc. Detailed protocols for producing such replication-defective recombinant viruses may be found for instance in WO 95/14785, WO 96/22378, U.S. Pat. Nos. 5,882,877, 6,013,516, 4,861,719, 5,278,056 and WO 94/19478.

A further object of the present invention relates to a host cell which has been transfected, infected or transformed by a nucleic acid and/or a vector according to the invention. As used herein, the term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA bas been "transformed".

The nucleic acids of the invention may be used to produce an antibody of the present invention in a suitable expression system. The term "expression system" means a host cell and compatible vector under suitable conditions, e.g. for the expression of a protein coded for by foreign DNA carried by the vector and introduced to the host cell. Common expression systems include *E. coli* host cells and plasmid vectors, insect host cells and Baculovirus vectors, and mammalian host cells and vectors. Other examples of host cells include, without limitation, prokaryotic cells (such as bacteria) and eukaryotic cells (such as yeast cells, mammalian cells, insect cells, plant cells, etc.). Specific examples include *E. coli*, *Kluyveromyces* or *Saccharomyces* yeasts, mammalian cell lines (e.g., Vero cells, CHO cells, 3T3 cells, COS cells, etc.) as well as primary or established mammalian cell cultures (e.g., produced from lymphoblasts, fibroblasts, embryonic cells, epithelial cells, nervous cells, adipocytes, etc.). Examples also include mouse SP2/0-Ag14 cell (ATCC CRL1581), mouse P3X63-Ag8.653 cell (ATCC CRL1580), CHO cell in which a dihydrofolate reductase gene (hereinafter referred to as "DHFR gene") is defective (Urlaub G et al; 1980), rat YB2/3HL.P2.G11.16Ag.20 cell (ATCC CRL1662, hereinafter referred to as "YB2/0 cell"), and the like. The present invention also relates to a method of producing a recombinant host cell expressing an antibody according to the invention, said method comprising the steps of: (i) introducing in vitro or ex vivo a recombinant nucleic acid or a vector as described above into a competent host cell, (ii) culturing in vitro or ex vivo the recombinant host cell obtained and (iii), optionally, selecting the cells which express and/or secrete said antibody. Such recombinant host cells can be used for the production of antibodies of the present invention.

Antibodies of the present invention are suitably separated from the culture medium by conventional immunoglobulin purification procedures such as, for example, protein A-Sepharose, hydroxylapatite chromatography, gel electrophoresis, dialysis, or affinity chromatography.

In some embodiments, the human chimeric antibody of the present invention can be produced by obtaining nucleic sequences encoding VL and VH domains as previously described, constructing a human chimeric antibody expression vector by inserting them into an expression vector for animal cell having genes encoding human antibody CH and human antibody CL, and expressing the coding sequence by introducing the expression vector into an animal cell. As the CH domain of a human chimeric antibody, it may be any region which belongs to human immunoglobulin, but those of IgG class are suitable and any one of subclasses belonging to IgG class, such as IgG1, IgG2, IgG3 and IgG4, can also be used. Also, as the CL of a human chimeric antibody, it may be any region which belongs to Ig, and those of kappa class or lambda class can be used. Methods for producing chimeric antibodies involve conventional recombinant DNA and gene transfection techniques are well known in the art (See Morrison S L. et al. (1984) and patent documents U.S. Pat. Nos. 5,202,238; and 5,204,244).

The humanized antibody of the present invention may be produced by obtaining nucleic acid sequences encoding CDR domains, as previously described, constructing a humanized antibody expression vector by inserting them into an expression vector for animal cell having genes encoding (i) a heavy chain constant region identical to that of a human antibody and (ii) a light chain constant region identical to that of a human antibody, and expressing the genes by introducing the expression vector into an animal cell. The humanized antibody expression vector may be either of a type in which a gene encoding an antibody heavy chain and a gene encoding an antibody light chain exists on separate vectors or of a type in which both genes exist on the same vector (tandem type). In respect of easiness of construction of a humanized antibody expression vector, easiness of introduction into animal cells, and balance between the expression levels of antibody H and L chains in animal cells, humanized antibody expression vector of the tandem type is preferred. Examples of tandem type humanized antibody expression vector include pKANTEX93 (WO 97/10354), pEE18 and the like. Methods for producing humanized antibodies based on conventional recombinant DNA and gene transfection techniques are well known in the art (See, e. g., Riechmann L. et al. 1988; Neuberger M S. et al. 1985). Antibodies can be humanized using a variety of techniques known in the art including, for example, CDR-grafting (EP 239,400; PCT publication WO91/09967; U.S. Pat. Nos. 5,225,539; 5,530,101; and 5,585,089), veneering or resurfacing (EP 592,106; EP 519,596; Padlan E A (1991); Studnicka G M et al. (1994); Roguska M A. et al. (1994)), and chain shuffling (U.S. Pat. No. 5,565,332). The general recombinant DNA technology for preparation of such antibodies is also known (see European Patent Application EP 125023 and International Patent Application WO 96/02576).

The Fab of the present invention can be obtained by treating an antibody which specifically reacts with AMH with a protease, papaine. Also, the Fab can be produced by inserting DNA encoding Fab of the antibody into a vector for prokaryotic expression system, or for eukaryotic expression system, and introducing the vector into a procaryote or eucaryote (as appropriate) to express the Fab.

The F(ab')2 of the present invention can be obtained treating an antibody which specifically reacts with AMH with a protease, pepsin. Also, the F(ab')2 can be produced by binding Fab' described below via a thioether bond or a disulfide bond.

The Fab' of the present invention can be obtained treating F(ab')2 which specifically reacts with AMH with a reducing agent, dithiothreitol. Also, the Fab' can be produced by inserting DNA encoding Fab' fragment of the antibody into an expression vector for prokaryote, or an expression vector for eukaryote, and introducing the vector into a prokaryote or eukaryote (as appropriate) to perform its expression.

The scFv of the present invention can be produced by obtaining cDNA encoding the VH and VL domains as previously described, constructing DNA encoding scFv, inserting the DNA into an expression vector for prokaryote, or an expression vector for eukaryote, and then introducing the expression vector into a prokaryote or eukaryote (as appropriate) to express the scFv. To generate a humanized scFv fragment, a well known technology called CDR grafting may be used, which involves selecting the complementary determining regions (CDRs) from a donor scFv fragment, and grafting them onto a human scFv fragment framework of known three dimensional structure (see, e. g., WO98/45322; WO 87/02671; U.S. Pat. Nos. 5,859,205; 5,585,089; 4,816,567; EP0173494).

Engineered antibodies of the present invention include those in which modifications have been made to framework residues within VH and/or VL, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis or PCR-mediated mutagenesis. Such "backmutated" antibodies are also intended to be encompassed by the invention. Another type of framework modification involves mutating one or more residues within the framework region, or even within one or more CDR regions, to remove T cell-epitopes to thereby reduce the potential immunogenicity of the antibody. This approach is also referred to as "deimmunization" and is described in further detail in U.S. Patent Publication No. 20030153043 by Carr et al.

The antibody of the invention can be characterized by one or more of the functional or structural features of the aspects described above, or by any combination of selected functional and structural features.

The antibody of the invention may be of any isotype. The choice of isotype typically will be guided by the desired effector functions, such as ADCC induction. Exemplary isotypes are IgG1, IgG2, IgG3, and IgG4. Either of the human light chain constant regions, kappa or lambda, may be used. If desired, the class of an antibody of the present invention may be switched by known methods. Typical, class switching techniques may be used to convert one IgG subclass to another, for instance from IgG1 to IgG2. Thus, the effector function of the antibodies of the present invention may be changed by isotype switching to, e.g., an IgG1, IgG2, IgG3, IgG4, IgD, IgA, IgE, or IgM antibody for various therapeutic uses. In some embodiments, the antibody of the invention is a full-length antibody. In some embodiments, the full-length antibody is an IgG1 antibody. In some embodiments, the full-length antibody is an IgG4 antibody. In some embodiments, the Nectin-4-specific IgG4 antibody is a stabilized IgG4 antibody. Examples of suitable stabilized IgG4 antibodies are antibodies wherein arginine at position 409 in a heavy chain constant region of human IgG4, which is indicated in the EU index as in Kabat et al. supra, is substituted with lysine, threonine, methionine, or leucine, preferably lysine (described in WO2006033386) and/or wherein the hinge region comprises a Cys-Pro-Pro-Cys sequence. Other suitable stabilized IgG4 antibodies are disclosed in WO2008145142, which is hereby incorporated by reference in its entirety. In some embodiments, the antibody of the present invention is an antibody of a non-IgG4 type, e.g. IgG1, IgG2 or IgG3 which has been mutated such that the ability to mediate effector functions, such as ADCC, has been reduced or even eliminated. Such mutations have e.g. been described in Dall'Acqua W F et al., J Immunol. 177(2): 1129-1138 (2006) and Hezareh M, J Virol. 75(24): 12161-12168 (2001).

In addition or alternative to modifications made within the framework or CDR regions, antibodies of the present invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the present invention may be chemically modified (e.g., one or more chemical moieties can be attached to the antibody) or be modified to alter its glycosylation, again to alter one or more functional properties of the antibody. For example, it will be appreciated that the affinity of antibodies provided by the present invention may be altered using any suitable method known in the art. The present invention therefore also relates to variants of the antibody molecules of the present invention, which have an improved affinity for Nectin-4. Such variants can be obtained by a number of affinity maturation protocols including mutating the CDRs (Yang et al., J. Mol. Biol., 254, 392-403, 1995), chain shuffling (Marks et al., Bio/Technology, 10, 779-783, 1992), use of mutator strains of E. coli (Low et al., J. Mol. Biol., 250, 359-368, 1996), DNA shuffling (Patten et al., Curr. Opin. Biotechnol., 8, 724-733, 1997), phage display (Thompson et al., J. Mol. Biol., 256, 77-88, 1996) and sexual PCR (Crameri et al., Nature, 391, 288-291, 1998). Vaughan et al. (supra) discusses these methods of affinity maturation.

In some embodiments, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In some embodiments, the antibody of the present invention is modified to increase its biological half-life. Various approaches are possible. For example, one or more of the following mutations can be introduced: T252L, T254S, T256F, as described in U.S. Pat. No. 6,277,375 by Ward. Alternatively, to increase the biological half-life, the antibody can be altered within the CHI or CL region to contain a salvage receptor binding epitope taken from two loops of a CH2 domain of an Fc region of an IgG, as described in U.S. Pat. Nos. 5,869,046 and 6,121,022 by Presta et al.

In some embodiments, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the CI component of complement. This approach is described in further detail in U.S. Pat. Nos. 5,624,821 and 5,648,260, both by Winter et al.

In some embodiments, one or more amino acids selected from amino acid residues can be replaced with a different amino acid residue such that the antibody has altered C1q binding and/or reduced or abolished complement dependent cytotoxicity (CDC). This approach is described in further detail in U.S. Pat. No. 6,194,551.

In some embodiments, one or more amino acid residues are altered to thereby alter the ability of the antibody to fix complement. This approach is described further in PCT Publication WO 94/29351 by Bodmer et al. In yet another embodiment, the Fc region is modified to increase the ability of the antibody to mediate antibody dependent cellular cytotoxicity (ADCC) and/or to increase the affinity of the antibody for an Fc receptor by modifying one or more amino acids. This approach is described further in PCT Publication WO 00/42072 by Presta. Moreover, the binding sites on human IgGI for FcγRI, FcγRII, FcγRIII and FcRn have been mapped and variants with improved binding have been described (see Shields, R. L. et al, 2001 J. Biol. Chen. 276:6591-6604, WO2010106180).

In some embodiments, the glycosylation of the antibody is modified. For example, an aglycoslated antibody can be made (i.e., the antibody lacks glycosylation). Glycosylation can be altered to, for example, increase the affinity of the antibody for the antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al. Additionally or alternatively, an antibody can be made that has an altered type of glycosylation, such as a hypofucosylated or non-fucosylated antibody having reduced amounts of or no fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the present invention to thereby produce an antibody with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation or are devoid of fucosyl residues. Therefore, in some embodiments, the antibodies of the present invention may be produced by recombinant expression in a cell line which exhibit hypofucosylation or non-fucosylation pattern, for example, a mammalian cell line with deficient expression of the FUT8 gene encoding fucosyltransferase. PCT Publication WO 03/035835 by Presta describes a variant CHO cell line, Lecl3 cells, with reduced ability to attach fucose to Asn(297)-linked carbohydrates, also resulting in hypofucosylation of antibodies expressed in that host cell (see also Shields, R. L. et al, 2002 J. Biol. Chem. 277:26733-26740). PCT Publication WO 99/54342 by Umana et al. describes cell lines engineered to express glycoprotein-modifying glycosyl transferases (e.g., beta(1,4)-N acetylglucosaminyl-transferase III (GnTIII)) such that antibodies expressed in the engineered cell lines exhibit increased bisecting GlcNac structures which results in increased ADCC activity of the antibodies (see also Umana et al, 1999 Nat. Biotech. 17: 176-180). Eureka Therapeutics further describes genetically engineered CHO mammalian cells capable of producing antibodies with altered mammalian glycosylation pattern devoid of fucosyl residues (http://www.eurekainc.com/a&boutus/companyoverview.html). Alternatively, the antibodies of the present invention can be produced in yeasts or filamentous fungi engineered for mammalian-like glycosylation pattern and capable of producing antibodies lacking fucose as glycosylation pattern (see for example EP1297172B1).

Another modification of the antibodies herein that is contemplated by the invention is pegylation. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. The pegylation can be carried out by an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (CI-CIO) alkoxy- or aryloxy-poly ethylene glycol or polyethylene glycol-maleimide. In some embodiments, the antibody to be pegylated is an aglycosylated antibody. Methods for pegylating proteins are known in the art and can be applied to the antibodies of the present invention. See for example, EP 0 154 316 by Nishimura et al. and EP 0 401 384 by Ishikawa et al.

Another modification of the antibodies that is contemplated by the invention is a conjugate or a protein fusion of at least the antigen-binding region of the antibody of the present invention to serum protein, such as human serum albumin or a fragment thereof to increase half-life of the resulting molecule. Such approach is for example described in Ballance et al. EP0322094.

In some embodiments, the invention provides a multispecific antibody comprising a first antigen binding site from an antibody of the present invention molecule described herein above and at least one second antigen binding site. In some embodiments, the second antigen-binding site is used for recruiting a killing mechanism such as, for example, by binding an antigen on a human effector cell or by binding a cytotoxic agent or a second therapeutic agent. As used herein, the term "effector cell" refers to an immune cell which is involved in the effector phase of an immune response, as opposed to the cognitive and activation phases of an immune response. Exemplary immune cells include a cell of a myeloid or lymphoid origin, for instance lymphocytes (such as B cells and T cells including cytolytic T cells (CTLs)), killer cells, natural killer cells, macrophages, monocytes, mast cells and granulocytes, such as neutrophils, eosinophils and basophils. Some effector cells express specific Fc receptors (FcRs) and carry out specific immune functions. In some embodiments, an effector cell is capable of inducing ADCC, such as a natural killer cell. For example, monocytes, macrophages, which express FcRs, are involved in specific killing of target cells and presenting antigens to other components of the immune system. In some embodiments, an effector cell may phagocytose a target antigen or target cell. The expression of a particular FcR on an effector cell may be regulated by humoral factors such as cytokines. An effector cell can phagocytose a target antigen or phagocytose or lyse a target cell. Suitable cytotoxic agents and second therapeutic agents are exemplified below, and include toxins (such as radiolabeled peptides), chemotherapeutic agents and prodrugs.

In some embodiments, the second antigen-binding site binds to an antigen on a human B cell, such as, e.g., CD19, CD20, CD21, CD22, CD23, CD46, CD80, CD138 and HLA-DR.

In some embodiments, the second antigen-binding site binds a tissue-specific antigen, promoting localization of the bispecific antibody to a specific tissue.

In some embodiments, the second antigen-binding site binds to an antigen located on the same type of cell as the Nectin-4-expressing cell, typically a tumor-associated antigen (TAA), but has a binding specificity different from that of the first antigen-binding site. Such multi- or bispecific antibodies can enhance the specificity of the tumor cell binding and/or engage multiple effector pathways. Exemplary TAAs include carcinoembryonic antigen (CEA), prostate specific antigen (PSA), RAGE (renal antigen), a-fetoprotein, CAMEL (CTL-recognized antigen on melanoma), CT antigens (such as MAGE-B5, -B6, -C2, -C3, and D; Mage-12; CT10; NY-ESO-1, SSX-2, GAGE, BAGE, MAGE, and SAGE), mucin antigens (e.g., MUC1, mucin-CA125, etc.), ganglioside antigens, tyrosinase, gp75, c-Met, Marti, MelanA, MUM-1, MUM-2, MUM-3, HLA-B7, Ep-CAM or a cancer-associated integrin, such as α5β3 integrin. Alternatively, the second antigen-binding site binds to a different epitope of Nectin-4. The second antigen-binding site may alternatively bind an angiogenic factor or other cancer-associated growth factor, such as a vascular endothelial growth factor, a fibroblast growth factor, epidermal growth factor, angiogenin or a receptor of any of these, particularly receptors associated with cancer progression.

In some embodiments, the second antigen-binding site is from a second human monoclonal antibody or ADC of the invention, such as the antibody of the present invention.

Exemplary formats for the multispecific antibody molecules of the invention include, but are not limited to (i) two antibodies cross-linked by chemical heteroconjugation, one with a specificity to Nectin-4 and another with a specificity to a second antigen; (ii) a single antibody that comprises two different antigen-binding regions; (iii) a single-chain antibody that comprises two different antigen-binding regions, e.g., two scFvs linked in tandem by an extra peptide linker; (iv) a dual-variable-domain antibody (DVD-Ig), where each light chain and heavy chain contains two variable domains in tandem through a short peptide linkage (Wu et al., Generation and Characterization of a Dual Variable Domain Immunoglobulin (DVD-Ig™) Molecule, In: Antibody Engineering, Springer Berlin Heidelberg (2010)); (v) a chemically-linked bispecific (Fab')2 fragment; (vi) a Tandab, which is a fusion of two single chain diabodies resulting in a tetravalent bispecific antibody that has two binding sites for each of the target antigens; (vii) a flexibody, which is a combination of scFvs with a diabody resulting in a multivalent molecule; (viii) a so called "dock and lock" molecule, based on the "dimerization and docking domain" in Protein Kinase A, which, when applied to Fabs, can yield a trivaient bispecific binding protein consisting of two identical Fab fragments linked to a different Fab fragment; (ix) a so-called Scorpion molecule, comprising, e.g., two scFvs fused to both termini of a human Fab-arm; and (x) a diabody. Another exemplary format for bispecific antibodies is IgG-like molecules with complementary CH3 domains to force heterodimerization. Such molecules can be prepared using known technologies, such as, e.g., those known as Triomab/Quadroma (Trion Pharma/Fresenius Biotech), Knob-into-Hole (Genentech), CrossMAb (Roche) and electrostatically-matched (Amgen), LUZ-Y (Genentech), Strand Exchange Engineered Domain body (SEEDbody)(EMD Serono), Biclonic (Merus) and DuoBody (Genmab A/S) technologies.

In some embodiments, the bispecific antibody is obtained or obtainable via a controlled Fab-arm exchange, typically using DuoBody technology. In vitro methods for producing bispecific antibodies by controlled Fab-arm exchange have been described in WO2008119353 and WO 2011131746 (both by Genmab A/S). In one exemplary method, described in WO 2008119353, a bispecific antibody is formed by "Fab-arm" or "half-molecule" exchange (swapping of a heavy chain and attached light chain) between two monospecific antibodies, both comprising IgG4-like CH3 regions, upon incubation under reducing conditions. The resulting product is a bispecific antibody having two Fab arms which may comprise different sequences. In another exemplary method, described in WO 2011131746, bispecific antibodies of the present invention are prepared by a method comprising the following steps, wherein at least one of the first and second antibodies is the antibody of the present invention: a) providing a first antibody comprising an Fc region of an immunoglobulin, said Fc region comprising a first CH3 region; b) providing a second antibody comprising an Fc region of an immunoglobulin, said Fc region comprising a second CH3 region; wherein the sequences of said first and second CH3 regions are different and are such that the heterodimeric interaction between said first and second CH3 regions is stronger than each of the homodimeric interactions of said first and second CH3 regions; c) incubating said first antibody together with said second antibody under reducing conditions; and d) obtaining said bispecific antibody, wherein the first antibody is the antibody of the present invention and the second antibody has a different binding specificity, or vice versa. The reducing conditions may, for example, be provided by adding a reducing agent, e.g. selected from 2-mercaptoethylamine, dithiothreitol and tris(2-carboxyethyl)phosphine. Step d) may further comprise restoring the conditions to become non-reducing or less reducing, for example by removal of a reducing agent, e.g. by desalting. Preferably, the sequences of the first and second CH3 regions are different, comprising only a few, fairly conservative, asymmetrical mutations, such that the heterodimeric interaction between said first and second CH3 regions is stronger than each of the homodimeric interactions of said first and second CH3 regions. More details on these interactions and how they can be achieved are provided in WO 2011131746, which is hereby incorporated by reference in its entirety. The following are exemplary embodiments of combinations of such assymetrical mutations, optionally wherein one or both Fc-regions are of the IgG1 isotype.

In some embodiments, the first Fc region has an amino acid substitution at a position selected from the group consisting of: 366, 368, 370, 399, 405, 407 and 409, and the second Fc region has an amino acid substitution at a position selected from the group consisting of: 366, 368, 370, 399, 405, 407 and 409, and wherein the first and second Fc regions are not substituted in the same positions.

In some embodiments, the first Fc region has an amino acid substitution at position 405, and said second Fc region has an amino acid substitution at a position selected from the group consisting of: 366, 368, 370, 399, 407 and 409, optionally 409.

In some embodiments, the first Fc region has an amino acid substitution at position 409, and said second Fc region has an amino acid substitution at a position selected from the group consisting of: 366, 368, 370, 399, 405, and 407, optionally 405 or 368.

In some embodiments, both the first and second Fc regions are of the IgG1 isotype, with the first Fc region having a Leu at position 405, and the second Fc region having an Arg at position 409.

In some embodiments, the antibody of the present invention is conjugated to a therapeutic moiety, i.e. a drug. The therapeutic moiety can be, e.g., a cytotoxin, a chemotherapeutic agent, a cytokine, an immunosuppressant, an immune stimulator, a lytic peptide, or a radioisotope. Such conjugates are referred to herein as an "antibody-drug conjugates" or "ADCs".

In some embodiments, the antibody is conjugated to a cytotoxic moiety. The cytotoxic moiety may, for example, be selected from the group consisting of taxol; cytochalasin B; gramicidin D; ethidium bromide; emetine; mitomycin; etoposide; tenoposide; vincristine; vinblastine; colchicin; doxorubicin; daunorubicin; dihydroxy anthracin dione; a tubulin-inhibitor such as maytansine or an analog or derivative thereof; an antimitotic agent such as monomethyl auristatin E or F or an analog or derivative thereof; dolastatin 10 or 15 or an analogue thereof; irinotecan or an analogue thereof; mitoxantrone; mithramycin; actinomycin D; 1-dehydrotestosterone; a glucocorticoid; procaine; tetracaine; lidocaine; propranolol; puromycin; calicheamicin or an analog or derivative thereof; an antimetabolite such as methotrexate, 6 mercaptopurine, 6 thioguanine, cytarabine, fludarabin, 5 fluorouracil, decarbazine, hydroxyurea, asparaginase, gemcitabine, or cladribine; an alkylating agent such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C; a platinum derivative such as cisplatin or carboplatin; duocarmycin A, duocarmycin SA, rachelmycin (CC-1065), or an analog or derivative thereof; an antibiotic such as dactinomycin, bleomycin, daunorubicin, doxorubicin, idarubicin, mithramycin, mitomycin, mitoxantrone, plicamycin, anthramycin (AMC)); pyrrolo[2,1-c][1,4]-benzodiazepines (PDB); diphtheria toxin and related molecules such as diphtheria A chain and active fragments thereof and hybrid molecules, ricin toxin such as ricin A or a deglycosylated ricin A chain toxin, cholera toxin, a Shiga-like toxin such as SLT I, SLT II, SLT IIV, LT toxin, C3 toxin, Shiga toxin, pertussis toxin, tetanus toxin, soybean Bowman-Birk protease inhibitor, *Pseudomonas* exotoxin, alorin, saporin, modeccin, gelanin, abrin A chain, modeccin A chain, alpha-sarcin, *Aleurites fordii* proteins, dianthin proteins, *Phytolacca americana* proteins such as PAPI, PAPII, and PAP-S, *Momordica charantia* inhibitor, curcin, crotin, *Sapaonaria officinalis* inhibitor, gelonin, mitogellin, restrictocin, phenomycin, and enomycin toxins; ribonuclease (RNase); DNase I, Staphylococcal enterotoxin A; pokeweed antiviral protein; diphtherin toxin; and *Pseudomonas* endotoxin.

In some embodiments, the antibody is conjugated to an auristatin or a peptide analog, derivative or prodrug thereof. Auristatins have been shown to interfere with microtubule dynamics, GTP hydrolysis and nuclear and cellular division (Woyke et al (2001) Antimicrob. Agents and Chemother. 45(12): 3580-3584) and have anti-cancer (U.S. Pat. No. 5,663,149) and antifungal activity (Pettit et al., (1998) Antimicrob. Agents and Chemother. 42: 2961-2965. For example, auristatin E can be reacted with para-acetyl benzoic acid or benzoylvaleric acid to produce AEB and AEVB, respectively. Other typical auristatin derivatives include AFP, MMAF (monomethyl auristatin F), and MMAE (monomethyl auristatin E). Suitable auristatins and auristatin analogs, derivatives and prodrugs, as well as suitable linkers for conjugation of auristatins to Abs, are described in, e.g., U.S. Pat. Nos. 5,635,483, 5,780,588 and 6,214,345 and in International patent application publications WO02088172, WO2004010957, WO2005081711, WO2005084390, WO2006132670, WO03026577, WO200700860, WO207011968 and WO205082023.

In some embodiments, the antibody is conjugated to Mertansine (also called emtansine or DM1) or a peptide analog, derivative or prodrug thereof. Mertansine is a tubulin inhibitor, meaning that it inhibits the assembly of microtubules by binding to tubulin.

In some embodiments, the antibody is conjugated to pyrrolo[2,1-c][1,4]-benzodiazepine (PDB) or an analog, derivative or prodrug thereof. Suitable PDBs and PDB derivatives, and related technologies are described in, e.g., Hartley J. A. et al., Cancer Res 2010; 70(17): 6849-6858; Antonow D. et al., Cancer J 2008; 14(3): 154-169; Howard P. W. et al., Bioorg Med Chem Lett 2009; 19: 6463-6466 and Sagnou et al., Bioorg Med Chem Lett 2000; 10(18): 2083-2086.

In some embodiments, the antibody is conjugated to a cytotoxic moiety selected from the group consisting of an anthracycline, maytansine, calicheamicin, duocarmycin, rachelmycin (CC-1065), dolastatin 10, dolastatin 15, irinotecan, monomethyl auristatin E, monomethyl auristatin F, a PDB, or an analog, derivative, or prodrug of any thereof.

In some embodiments, the antibody is conjugated to an anthracycline or an analog, derivative or prodrug thereof. In some embodiments, the antibody is conjugated to maytansine or an analog, derivative or prodrug thereof. In some embodiments, the antibody is conjugated to calicheamicin or an analog, derivative or prodrug thereof. In some embodiments, the antibody is conjugated to duocarmycin or an analog, derivative or prodrug thereof. In some embodiments, the antibody is conjugated to rachelmycin (CC-1065) or an analog, derivative or prodrug thereof. In some embodiments, the antibody is conjugated to dolastatin 10 or an analog, derivative or prodrug thereof. In some embodiments, the antibody is conjugated to dolastatin 15 or an analog, derivative or prodrug thereof. In some embodiments, the antibody is conjugated to monomethyl auristatin E or an analog, derivative or prodrug thereof. In some embodiments, the antibody is conjugated to monomethyl auristatin F or an analog, derivative or prodrug thereof. In some embodiments, the antibody is conjugated to pyrrolo[2,1-c][1,4]-benzodiazepine or an analog, derivative or prodrug thereof. In some embodiments, the antibody is conjugated to irinotecan or an analog, derivative or prodrug thereof.

In some embodiments, the antibody is conjugated to a nucleic acid or nucleic acid-associated molecule. In one such embodiment, the conjugated nucleic acid is a cytotoxic ribonuclease (RNase) or deoxy-ribonuclease (e.g., DNase I), an antisense nucleic acid, an inhibitory RNA molecule (e.g., a siRNA molecule) or an immunostimulatory nucleic acid (e.g., an immunostimulatory CpG motif-containing DNA molecule). In some embodiments, the antibody is conjugated to an aptamer or a ribozyme.

In some embodiments, the antibody is conjugated, e.g., as a fusion protein, to a lytic peptide such as CLIP, Magainin 2, mellitin, Cecropin and P18.

In some embodiments, the antibody is conjugated to a cytokine, such as, e.g., IL-2, IL-4, IL-6, IL-7, IL-10, IL-12, IL-13, IL-15, IL-18, IL-23, IL-24, IL-27, IL-28a, IL-28b, IL-29, KGF, IFNa, IFN3, IFNy, GM-CSF, CD40L, Flt3 ligand, stem cell factor, ancestim, and TNFa.

In some embodiments, the antibody is conjugated to a radioisotope or to a radioisotope-containing chelate. For example, the antibody can be conjugated to a chelator linker, e.g. DOTA, DTPA or tiuxetan, which allows for the antibody to be complexed with a radioisotope. The antibody may also or alternatively comprise or be conjugated to one or more radiolabeled amino acids or other radiolabeled molecules. Non-limiting examples of radioisotopes include $^{3}$H, $^{14}$C, $^{15}$N, $^{35}$S, $^{90}$Y, $^{99}$Tc, $^{125}$I, $^{131}$I, $^{186}$Re, $^{213}$Bi, $^{225}$Ac and $^{227}$Th. For therapeutic purposes, a radioisotope emitting beta- or alpha-particle radiation can be used, e.g., 1311, 90Y, 211At, 212Bi, 67Cu, 186Re, 188Re, and 212Pb.

Techniques for conjugating molecule to antibodies, are well-known in the art (See, e.g., Arnon et al., "Monoclonal Antibodies For Immunotargeting Of Drugs In Cancer Therapy," in Monoclonal Antibodies And Cancer Therapy (Reisfeld et al. eds., Alan R. Liss, Inc., 1985); Hellstrom et al., "Antibodies For Drug Delivery," in Controlled Drug Delivery (Robinson et al. eds., Marcel Deiker, Inc., 2nd ed. 1987); Thorpe, "Antibody Carriers Of Cytotoxic Agents In Cancer Therapy: A Review," in Monoclonal Antibodies '84: Biological And Clinical Applications (Pinchera et al. eds., 1985); "Analysis, Results, and Future Prospective of the Therapeutic Use of Radio labeled Antibody In Cancer Therapy," in Monoclonal Antibodies For Cancer Detection And Therapy (Baldwin et al. eds., Academic Press, 1985); and Thorpe et al., 1982, Immunol. Rev. 62:119-58. See also, e.g., PCT publication WO 89/12624.) Typically, the nucleic acid molecule is covalently attached to lysines or cysteines on the antibody, through N-hydroxysuccinimide ester or maleimide functionality respectively. Methods of conjugation using engineered cysteines or incorporation of unnatural amino acids have been reported to improve the homogeneity of the conjugate (Axup, J. Y., Bajjuri, K. M., Ritland, M., Hutchins, B. M., Kim, C. H., Kazane, S. A., Halder, R., Forsyth, J. S., Santidrian, A. F., Stafin, K., et al. (2012). Synthesis of site-specific antibody-drug conjugates using unnatural amino acids. Proc. Natl. Acad. Sci. USA 109, 16101-16106; Junutula, J. R., Flagella, K. M., Graham, R. A., Parsons, K. L., Ha, E., Raab, H., Bhakta, S., Nguyen, T., Dugger, D. L., Li, G., et al. (2010). Engineered thiotrastuzumab-DM1 conjugate with an improved therapeutic index to target humanepidermal growth factor receptor 2-positive breast cancer. Clin. Cancer Res. 16, 4769-4778). Junutula et al. (2008) developed cysteine-based site-specific conjugation called "THIOMABs" (TDCs) that are claimed to display an improved therapeutic index as compared to conventional conjugation methods. Conjugation to unnatural amino acids that have been incorporated into the antibody is also being explored for ADCs; however, the generality of this approach is yet to be established (Axup et al., 2012). In particular the one skilled in the art can also envisage Fc-containing polypeptide engineered with an acyl donor glutamine-containing tag (e.g., Gln-containing peptide tags or Q-tags) or an endogenous glutamine that are made reactive by polypeptide engineering (e.g., via amino acid deletion, insertion, substitution, or mutation on the polypeptide). Then a transglutaminase, can covalently cross-link with an amine donor agent (e.g., a small molecule comprising or attached to a reactive amine) to form a stable and homogenous population of an engineered Fc-containing polypeptide conjugate with the amine donor agent being site-specifically conjugated to the Fc-containing polypeptide through the acyl donor glutamine-containing tag or the accessible/exposed/reactive endogenous glutamine (WO 2012059882).

In another aspect, the invention relates to the antibody of the present invention, as defined in any aspect or embodiment herein, for use as a medicament.

The antibody of the present invention can be used in the treatment or prevention of disorders involving cells expressing Nectin-4.

As used herein, the term "treatment" or "treat" refer to both prophylactic or preventive treatment as well as curative or disease modifying treatment, including treatment of patient at risk of contracting the disease or suspected to have contracted the disease as well as patients who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a patient during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a patient during treatment of an illness, e.g., to keep the patient in remission for long periods of time (months or years). A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria [e.g., pain, disease manifestation, etc.]).

In some embodiments, the invention provides a method for killing a Nectin-4-expressing cell by contacting the cell with the antibody of the present invention. In some embodiments, the invention provides a method for killing a Nectin-4-expressing cell by contacting the cell with the antibody of the present invention in the presence of effector cells capable of inducing an Fc-mediated effector cell response such as a CDC, ADCC or ADCP response. In this embodiment, the antibody is typically full-length and of an isotype leading to a CDC or ADCC response, such as, e.g., an IgG1 isotype. In some embodiments, the invention provides a method for killing a Nectin-4-expressing cell by contacting the cell with an ADC of the invention.

In some embodiments, the antibody of the present invention is particularly suitable for the treatment of cancer. Cancer cells over-expressing Nectin-4 are indeed good targets for the antibodies of the present invention, since more antibodies may be bound per cell. Thus, in one aspect, the disorder involving cells expressing Nectin-4 is cancer, i.e., a tumorigenic disorder, such as a disorder characterized by the presence of tumor cells expressing Nectin-4 including, for example, disorders where the cells are from a solid tumor or hematological tumor. In particular, the antibody of the present invention may be used as treatment of hyperproliferative diseases associated with Nectin-4 expression, overexpression or activation. In particular, the antibody of the present invention is particularly suitable for the treatment of breast cancer, ovarian cancer and lung cancer. As used herein, the term "breast cancer" as used herein includes, but is not limited to, all types of breast cancers at all stages of progression like metastatic breast cancer or breast carcinomas. In particular, the breast cancer is selected among triple-negative breast cancers (TNBC) that are distinguished by negative immunohistochemical staining for estrogen and progesterone receptors and human epidermal growth factor receptor-2 (HER2), and represent 15% of all breast cancers. The term "ovarian cancer" as used herein includes, but is not limited to, all types of ovarian cancers at all stages of progression like metastatic ovarian cancer or ovarian carcinomas. The term "lung cancer" as used herein includes, but is not limited to all types of lung cancers at all stages of progression like lung carcinomas metastatic lung cancer, non-small cell lung carcinomas or Small cell lung carcinoma.

In some embodiments, the antibody of the present invention is particularly suitable for the treatment of a metastatic cancer.

A "therapeutically effective amount" refers to an amount effective, at dosages and for periods of time necessary, to achieve a desired therapeutic result. A therapeutically effective amount of the antibody of the present invention may vary according to factors such as the disease state, age, sex, and weight of the individual, and the ability of the antibody of the present invention to elicit a desired response in the individual. A therapeutically effective amount is also one in which any toxic or detrimental effects of the antibody or antibody portion are outweighed by the therapeutically beneficial effects. The efficient dosages and dosage regimens for the antibody of the present invention depend on the disease or condition to be treated and may be determined by the persons skilled in the art. A physician having ordinary skill in the art may readily determine and prescribe the effective amount of the pharmaceutical composition required. For example, the physician could start doses of the antibody of the present invention employed in the pharmaceutical composition at levels lower than that required in order to achieve the desired therapeutic effect and gradually increase the dosage until the desired effect is achieved. In general, a suitable dose of a composition of the present invention will be that amount of the compound which is the lowest dose effective to produce a therapeutic effect according to a particular dosage regimen. Such an effective dose will generally depend upon the factors described above. For example, a therapeutically effective amount for therapeutic use may be measured by its ability to stabilize the progression of disease. The ability of a compound to inhibit cancer may, for example, be evaluated in an animal model system predictive of efficacy in human tumors. Alternatively, this property of a composition may be evaluated by examining the ability of the compound to inhibit tumor cell growth by in vitro assays known to the skilled practitioner. A therapeutically effective amount of a therapeutic compound may decrease tumor size, or otherwise ameliorate symptoms in a subject. One of ordinary skill in the art would be able to determine such amounts based on such factors as the subject's size, the severity of the subject's symptoms, and the particular composition or route of administration selected. An exemplary, non-limiting range for a therapeutically effective amount of the antibody of the present invention is about 0.1-100 mg/kg, such as about 0.1-50 mg/kg, for example about 0.1-20 mg/kg, such as about 0.1-10 mg/kg, for instance about 0.5, about such as 0.3, about 1, about 3 mg/kg, about 5 mg/kg or about 8 mg/kg. An exemplary, non-limiting range for a therapeutically effective amount of an antibody of the present invention is 0.02-100 mg/kg, such as about 0.02-30 mg/kg, such as about 0.05-10 mg/kg or 0.1-3 mg/kg, for example about 0.5-2 mg/kg. Administration may e.g. be intravenous, intramuscular, intraperitoneal, or subcutaneous, and for instance administered proximal to the site of the target. Dosage regimens in the above methods of treatment and uses are adjusted to provide the optimum desired response (e.g., a therapeutic response). For example, a single bolus may be administered, several divided doses may be administered over time or the dose may be proportionally reduced or increased as indicated by the exigencies of the therapeutic situation. In some embodiments, the efficacy of the treatment is monitored during the therapy, e.g. at predefined points in time. In some embodiments, the efficacy may be monitored by measuring the level of Nectin-4 in a sample containing tumor cells, by visualization of the disease area, or by other diagnostic methods described further herein, e.g. by performing one or more PET-CT scans, for example using a labeled antibody of the present invention, fragment or mini-antibody derived from the antibody of the present invention. If desired, an effective daily dose of a pharmaceutical composition may be administered as two, three, four, five, six or more sub-doses administered separately at appropriate intervals throughout the day, optionally, in unit dosage forms. In some embodiments, the antibodies of the present invention are administered by slow continuous infusion over a long period, such as more than 24 hours, in order to minimize any unwanted side effects. An effective dose of the antibody of the present invention of the invention may also be administered using a weekly, biweekly or triweekly dosing period. The dosing period may be restricted to, e.g., 8 weeks, 12 weeks or until clinical progression has been established. As non-limiting examples, treatment according to the present invention may be provided as a daily dosage of a compound of the present invention in an amount of about 0.1-100 mg/kg, such as 0.2, 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of days 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of weeks 1, 2, 3, 4, 5, 6, 7, 8, 9, 10, 11, 12, 13, 14, 15, 16, 17, 18, 19 or 20 after initiation of treatment, or any combination thereof, using single or divided doses every 24, 12, 8, 6, 4, or 2 hours, or any combination thereof.

The invention also provides for therapeutic applications where the antibody of the present invention is used in combination with at least one further therapeutic agent relevant for the disease or disorder to be treated, as described above. Such administration may be simultaneous, separate or sequential. For simultaneous administration the agents may be administered as one composition or as separate compositions, as appropriate. The further therapeutic agent is typically relevant for the disorder to be treated. Exemplary therapeutic agents include other anti-cancer antibodies or ADCs, cytotoxic agents, chemotherapeutic agents, anti-angiogenic agents, anti-cancer immunogens, cell cycle control/apoptosis regulating agents, hormonal regulating agents, and other agents described below.

For administration, the antibody of the present invention is formulated as a pharmaceutical composition. A pharmaceutical composition comprising the antibody of the present invention can be formulated according to known methods to prepare pharmaceutically useful compositions, whereby the therapeutic molecule is combined in a mixture with a pharmaceutically acceptable carrier. A composition is said to be a "pharmaceutically acceptable carrier" if its administration can be tolerated by a recipient patient. Sterile phosphate-buffered saline is one example of a pharmaceutically acceptable carrier. Other suitable carriers are well-known to those in the art. (See, e.g., Gennaro (ed.), Remington's Pharmaceutical Sciences (Mack Publishing Company, 19th ed. 1995)) Formulations may further include one or more excipients, preservatives, solubilizers, buffering agents, albumin to prevent protein loss on vial surfaces, etc. The form of the pharmaceutical compositions, the route of administration, the dosage and the regimen naturally depend upon the condition to be treated, the severity of the illness, the age, weight, and sex of the patient, etc. The pharmaceutical compositions of the invention can be formulated for a topical, oral, parenteral, intranasal, intravenous, intramuscular, subcutaneous or intraocular administration and the like.

Typically, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The doses used for the administration can be adapted as a function of various parameters, and in particular as a function of the mode of administration used, of the relevant pathology, or alternatively of the desired duration of treatment.

To prepare pharmaceutical compositions, an effective amount of the antibody may be dissolved or dispersed in a pharmaceutically acceptable carrier or aqueous medium.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

An antibody of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly concentrated solutions for direct injection is also contemplated, where the use of DMSO as solvent is envisioned to result in extremely rapid penetration, delivering high concentrations of the active agents to a small tumor area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

The antibodies of the invention may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

In addition to the compounds formulated for parenteral administration, such as intravenous or intramuscular injection, other pharmaceutically acceptable forms include, e.g. tablets or other solids for oral administration; time release capsules; and any other form currently used.

In some embodiments, the use of liposomes and/or nanoparticles is contemplated for the introduction of antibodies into host cells. The formation and use of liposomes and/or nanoparticles are known to those of skill in the art.

Nanocapsules can generally entrap compounds in a stable and reproducible way. To avoid side effects due to intracellular polymeric overloading, such ultrafine particles (sized around 0.1 μm) are generally designed using polymers able to be degraded in vivo. Biodegradable polyalkyl-cyanoacrylate nanoparticles that meet these requirements are contemplated for use in the present invention, and such particles may be are easily made.

Liposomes are formed from phospholipids that are dispersed in an aqueous medium and spontaneously form multilamellar concentric bilayer vesicles (also termed multilamellar vesicles (MLVs)). MLVs generally have diameters of from 25 nm to 4 μm. Sonication of MLVs results in the formation of small unilamellar vesicles (SUVs) with diameters in the range of 200 to 500 Å, containing an aqueous solution in the core. The physical characteristics of liposomes depend on pH, ionic strength and the presence of divalent cations.

The present invention also provides chimeric antigen receptors (CARs) comprising an antigen binding domain of the antibody of the present invention. Typically, said chimeric antigen receptor comprises at least one VH and/or VL sequence of the antibody of the present invention. The chimeric antigen receptor the present invention also comprises an extracellular hinge domain, a transmembrane domain, and an intracellular T cell signaling domain.

As used herein, the term "chimeric antigen receptor" or "CAR" has its general meaning in the art and refers to an artificially constructed hybrid protein or polypeptide containing the antigen binding domains of an antibody (e.g., scFv) linked to T-cell signaling domains. Characteristics of CARs include their ability to redirect T-cell specificity and reactivity toward a selected target in a non-MHC-restricted manner, exploiting the antigen-binding properties of monoclonal antibodies. The non-MHC-restricted antigen recognition gives T cells expressing CARs the ability to recognize antigen independent of antigen processing, thus bypassing a major mechanism of tumor escape. Moreover, when expressed in T-cells, CARs advantageously do not dimerize with endogenous T cell receptor (TCR) alpha and beta chains.

In some embodiments, the invention provides CARs comprising an antigen-binding domain comprising, consisting of, or consisting essentially of, a single chain variable fragment (scFv) of the N41mab antibody. In some embodiments, the antigen binding domain comprises a linker peptide. The linker peptide may be positioned between the light chain variable region and the heavy chain variable region.

In some embodiments, the CAR comprises an extracellular hinge domain, a transmembrane domain, and an intracellular T cell signaling domain selected from the group consisting of CD28, 4-1BB, and CD3ζ intracellular domains. CD28 is a T cell marker important in T cell co-stimulation. 4-1BB transmits a potent costimulatory signal to T cells, promoting differentiation and enhancing long-term survival of T lymphocytes. CD3ζ associates with TCRs to produce a signal and contains immunoreceptor tyrosine-based activation motifs (ITAMs).

In some embodiments, the chimeric antigen receptor of the present invention can be glycosylated, amidated, carboxylated, phosphorylated, esterified, N-acylated, cyclized via, e.g., a disulfide bridge, or converted into an acid addition salt and/or optionally dimerized or polymerized.

The invention also provides a nucleic acid encoding for a chimeric antigen receptor of the present invention. In some embodiments, the nucleic acid is incorporated in a vector as such as described above.

The present invention also provides a host cell comprising a nucleic acid encoding for a chimeric antigen receptor of the present invention. While the host cell can be of any cell type, can originate from any type of tissue, and can be of any developmental stage, the host cell is a T cell, e.g. isolated from peripheral blood lymphocytes (PBL) or peripheral blood mononuclear cells (PBMC). In some embodiments, the T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. The T cell can be any type of T cell and can be of any developmental stage, including but not limited to, CD4+/CD8+ double positive T cells, CD4+ helper T cells, e.g., Th2 cells, CD8+ T cells (e.g., cytotoxic T cells), tumor infiltrating cells, memory T cells, naive T cells, and the like. The T cell may be a CD8+ T cell or a CD4+ T cell.

The population of those T cells prepared as described above can be utilized in methods and compositions for adoptive immunotherapy in accordance with known techniques, or variations thereof that will be apparent to those skilled in the art based on the instant disclosure. See, e.g., US Patent Application Publication No. 2003/0170238 to Gruenberg et al; see also U.S. Pat. No. 4,690,915 to Rosenberg. Adoptive immunotherapy of cancer refers to a therapeutic approach in which immune cells with an antitumor reactivity are administered to a tumor-bearing host, with the aim that the cells mediate either directly or indirectly, the regression of an established tumor. Transfusion of lymphocytes, particularly T lymphocytes, falls into this category. Currently, most adoptive immunotherapies are autolymphocyte therapies (ALT) directed to treatments using the patient's own immune cells. These therapies involve processing the patient's own lymphocytes to either enhance the immune cell mediated response or to recognize specific antigens or foreign substances in the body, including the cancer cells. The treatments are accomplished by removing the patient's lymphocytes and exposing these cells in vitro to biologics and drugs to activate the immune function of the cells. Once the autologous cells are activated, these ex vivo activated cells are reinfused into the patient to enhance the immune system to treat cancer. In some embodiments, the cells are formulated by first harvesting them from their culture medium, and then washing and concentrating the cells in a medium and container system suitable for administration (a "pharmaceutically acceptable" carrier) in a treatment-effective amount. Suitable infusion medium can be any isotonic medium formulation, typically normal saline, Normosol R (Abbott) or Plasma-Lyte A (Baxter), but also 5% dextrose in water or Ringer's lactate can be utilized. The infusion medium can be supplemented with human serum albumin. A treatment-effective amount of cells in the composition is dependent on the relative representation of the T cells with the desired specificity, on the age and weight of the recipient, on the severity of the targeted condition and on the immunogenicity of the targeted Ags. These amount of cells can be as low as approximately $10^3$/kg, preferably $5 \times 10^3$/kg; and as high as $10^7$/kg, preferably $10^8$/kg. The number of cells will depend upon the ultimate use for which the composition is intended, as will the type of cells included therein. For example, if cells that are specific for a particular Ag are desired, then the population will contain greater than 70%, generally greater than 80%, 85% and 90-95% of such cells. For uses provided herein, the cells are generally in a volume of a liter or less, can be 500 ml or less, even 250 ml or 100 ml or less. The clinically relevant number of immune cells can be apportioned into multiple infusions that cumulatively equal or exceed the desired total amount of cells.

In particular the cells of the present invention are particularly suitable for the treatment of cancer. According, a further object of the present invention relates to a method of treating cancer in a subject in need thereof comprising administering to the subject a therapeutically effective amount of a population of cells of the present invention.

The invention will be further illustrated by the following figures and examples. However, these examples and figures should not be interpreted in any way as limiting the scope of the present invention.

FIGURES

Figure 1B:
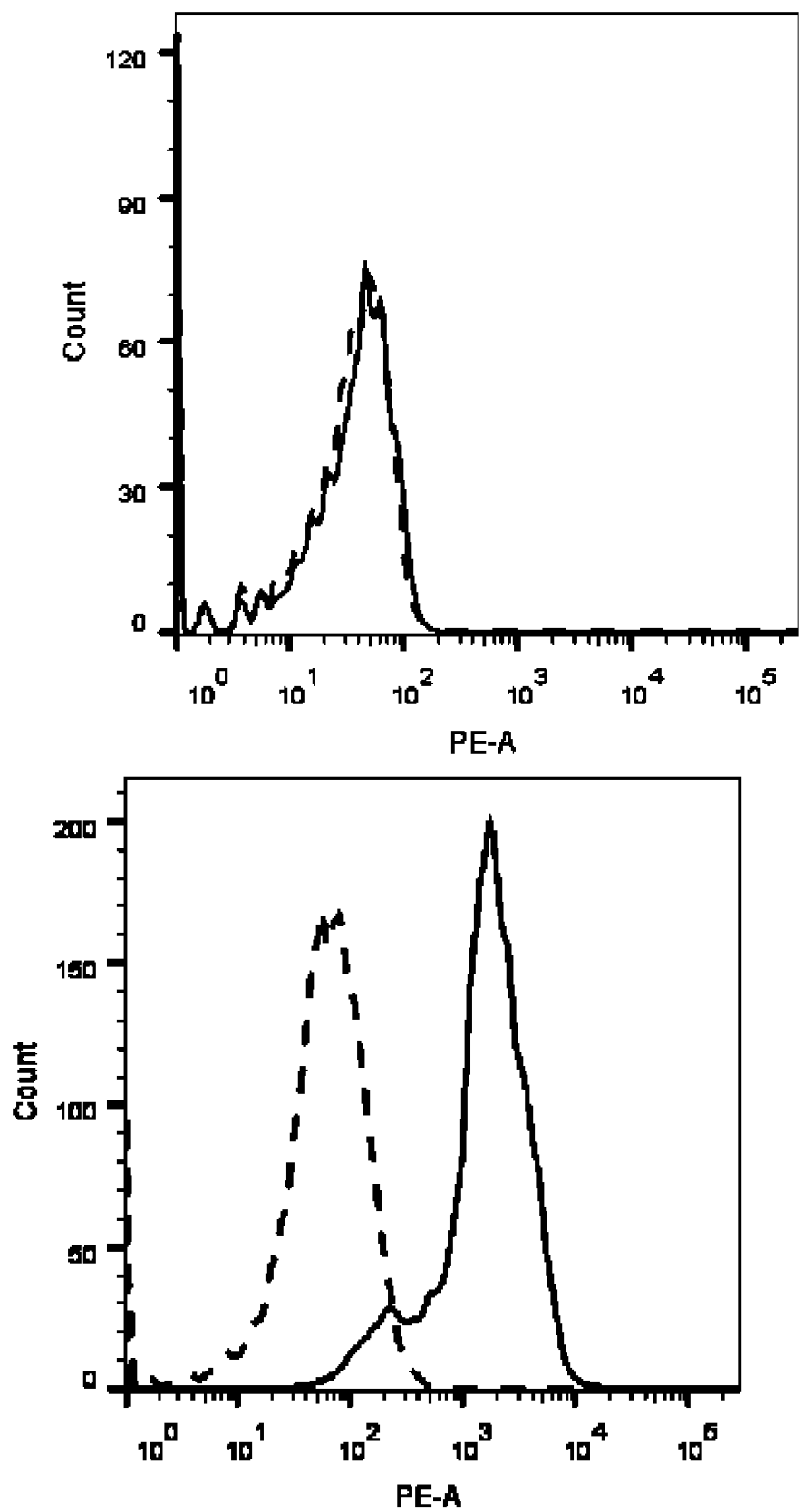

FIG. 1: N41mab recognizes IgV-like domain of nectin4

A: Detection by ELISA. Ninety-six-well trays were coated with 5 ug/ml of nectin4V-Fc or nectin1V-Fc (comprising only the IgV domain) overnight at +4° C. as indicated. N41mab recognizes the nectin4V-Fc (bar 3) not the nectin1V-Fc (bar 1).

B: Detection by FACS. FACS analysis of MDAMB231 cell line transfected with the N-terminal Flag-Tagged epitope of Nectin4 using 2 μg/ml N41mab antibody. Cells were then stained with phycoerythrin conjugate goat anti mouse antibody (Beckman-Coulter). Left: MDAMB231 cells, Right: MDAMB231 nectin4 cells. (--- Ctrl Ig) (-N41mab).

Figure 2:
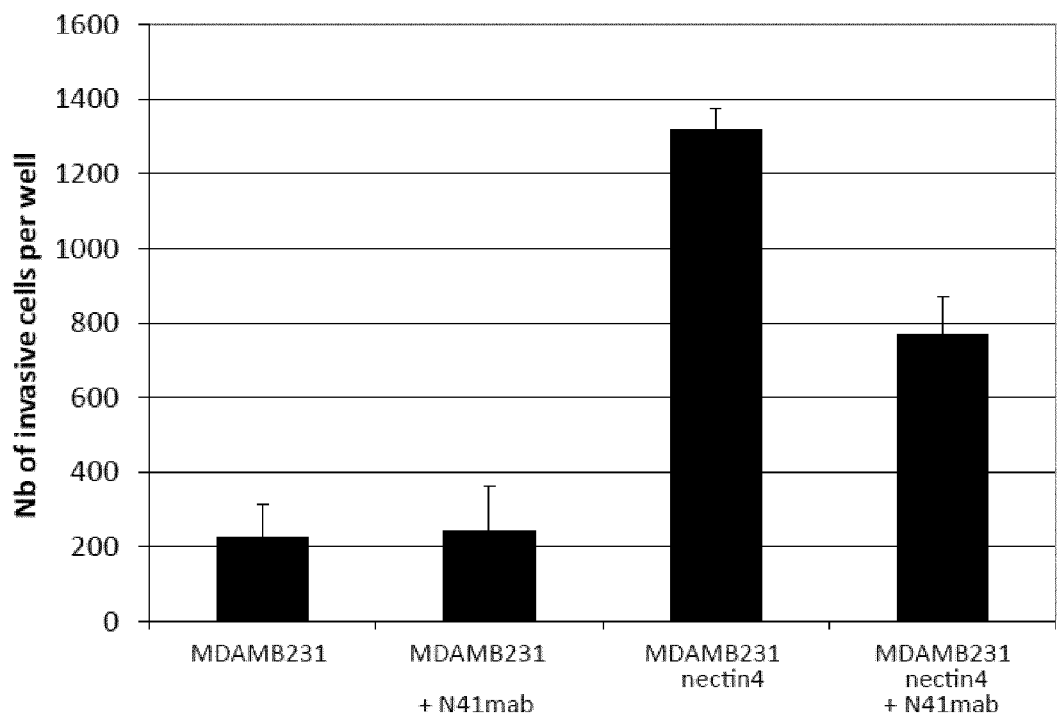

FIG. 2: N41mab blocks tumor cell invasion in vitro

Invasion was measured with the Matrigel coated invasion chamber. Ectopic expression of nectin4 markedly increases cell invasion (compare bar 1 to bar 3). Treatment of MDAMB231 nectin4 cells with 10 μg/ml N41mab prior to invasion assay, induces a 43% inhibition of invasion (compare bar 3 and bar 4). This result is representative of 3 experiments.

Figure 3:
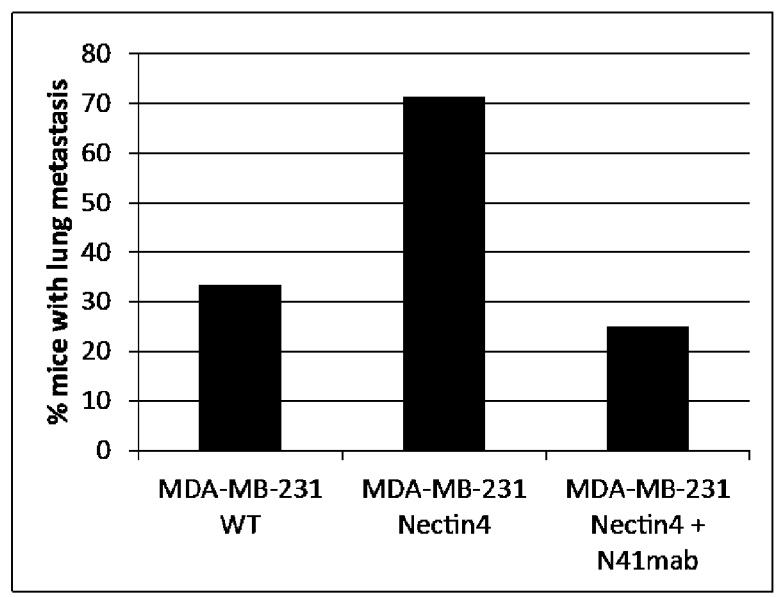

FIG. 3: N41mab inhibits metastatic progression from primary site in vivo

Luciferase expressing MDAMB231 and MDAMB231 nectin4 cells ($1 \times 10^6$ cells) were xenografted subcutaneously in NSG mice. N41mab (10 mg/kg) was injected IP every week. Bioluminescence analysis was performed at day 74 post-graft. Lungs are represented and percentage of positive organ mentioned in the presence and absence of treatment with N41mab.

Histogram resumes the data obtained. Treatment of NSG mice with N41mab reduces the percentage of mice with lung metastasis. From 71% to 25%. This result is representative of 2 experiments.

Figure 4:
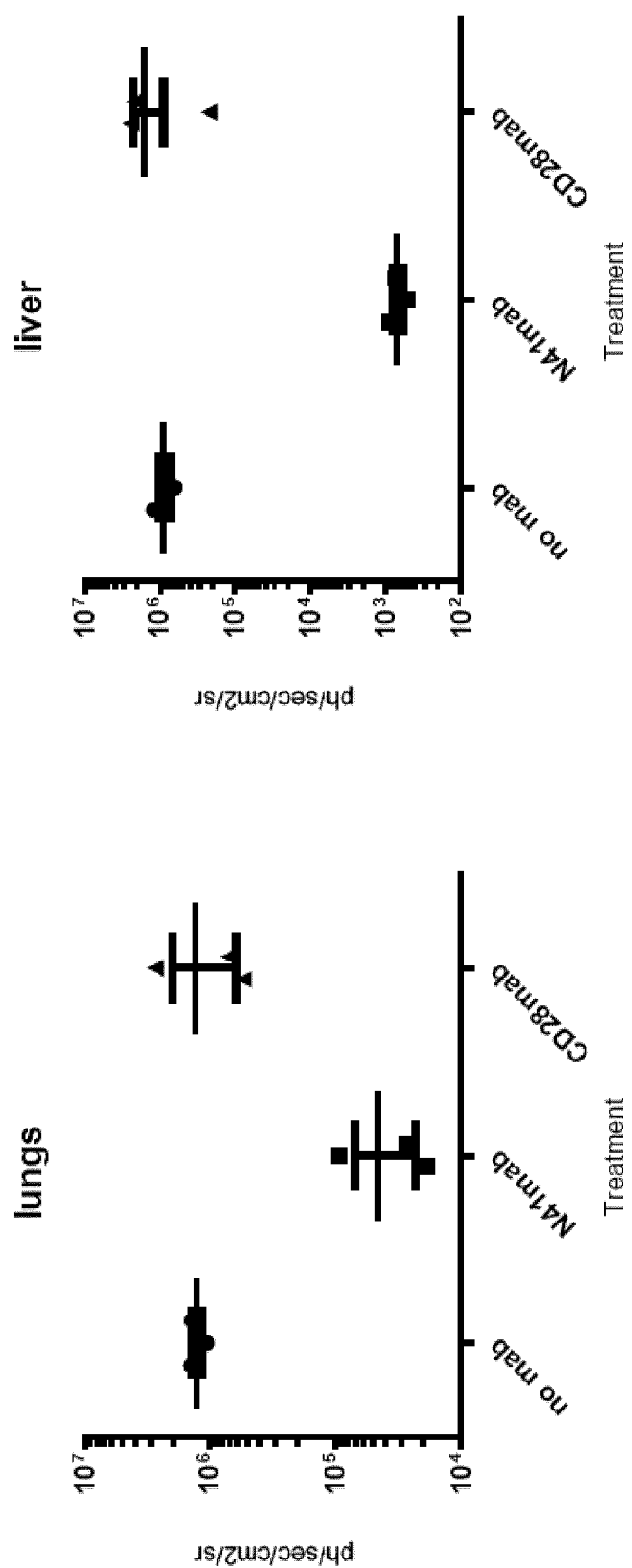

FIG. 4: N41mab inhibits metastasis homing in vivo

Luciferase expressing SUM190 cells ($0.5 \times 10^6$ cells) were injected in caudal vein in NSG mice. Mab treatment was performed by incubating cells with 10 μg/ml antibody and by treating cells with 10 mg/kg antibody. CD28 monoclonal antibody was used as control. Bioluminescence analysis of isolated organs at day 32 in lungs and liver; the two major sites of metastasis. This result is representative of two experiments. Similar results were obtained in NSG mice pretreated two days with 0.2 ml clodronate liposomes (macrophage depletion) (data not shown).

FIG. 5: N41mab EC50 determination

A: Cell surface binding of a serial dilution of N41mab was measured by FACS analysis on SUM190 cells (black). Comparison was done with the Ha22-2 anti nectin4 mab (white) (i.e. ASG-22ME).

B: Binding of N41mab on recombinant nectin4 VCC-Fc was done by ELISA (black). Comparison was done with the Ha22-2 anti nectin4 mab (white) (i.e. ASG-22ME).

Figure 6A:
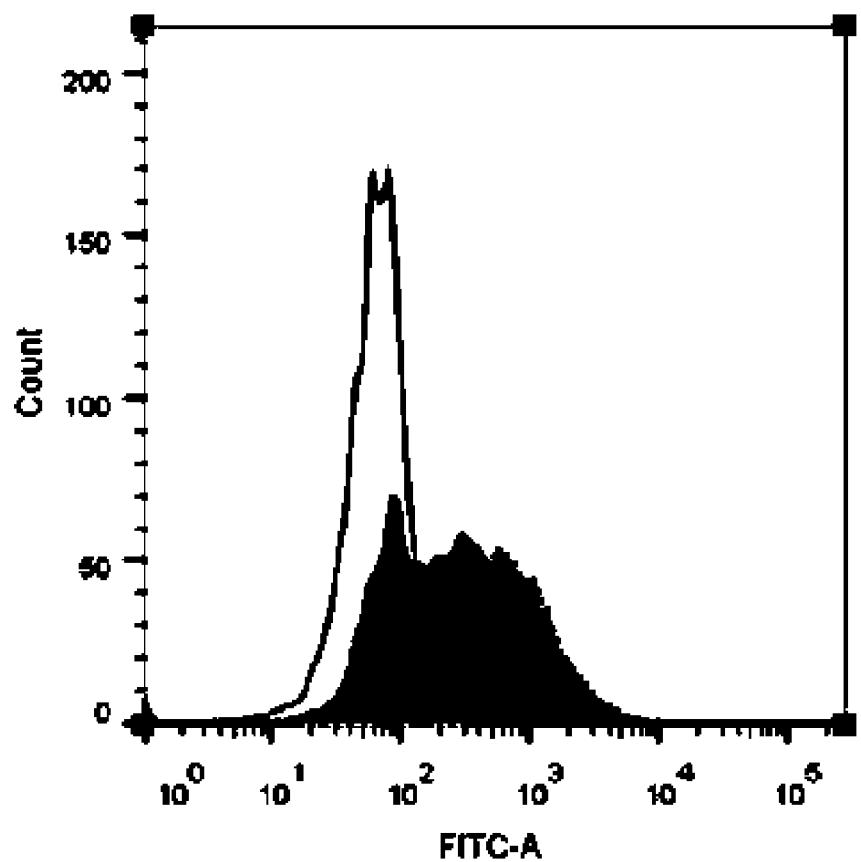
Figure 6B:
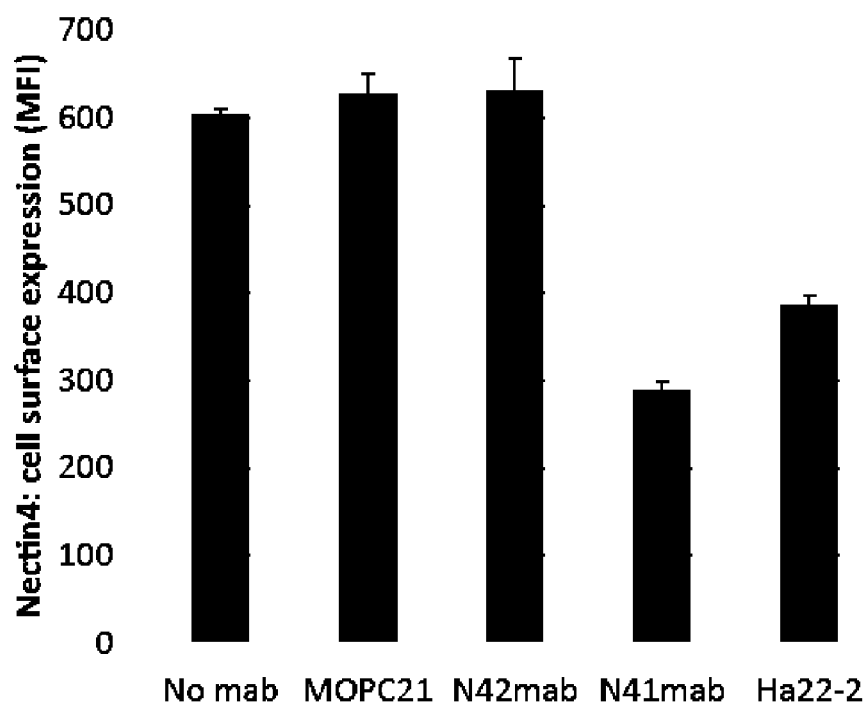

FIG. 6: N41mab internalization

Internalization was done using the epitope-FLAG tagged nectin4 expressed in MDAMB231 cells.

A: Cell surface expression of nectin4 by FACS. Cells were firstly incubated individually with the mabs for 24 h at 37° C. and cell surface expression was monitored using FITC-labelled anti-FLAG antibody (M2). Illustration: Bold grey: Ctrl Ig, dotted black: N42mab, bold black: N41mab. (N42mab is a control anti nectin4 mab directed against IgV domain)

B: Comparison of percentage of internalization induced by N42mab, N41mab and Ha22-2 mab done by FACS.

Figure 7:
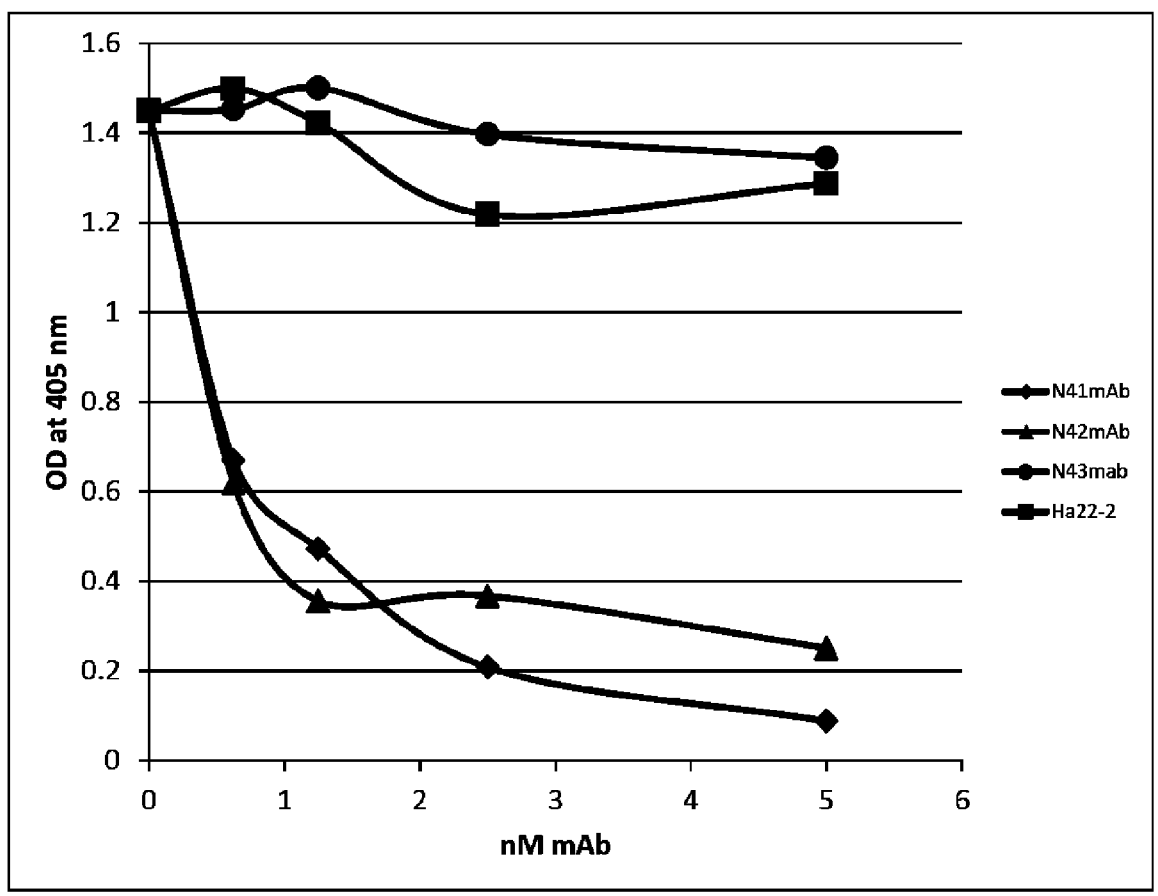

FIG. 7: Characterization of N41mab epitope

Mab competition assay was performed by ELISA. Ninety-six-well trays were coated with nectin4VCC-Fc overnight at +4° C. as indicated. Binding of peroxidase conjugated N41mab was measured in the presence of variable concentration of N41mab, N42mab, N43mab and Ha22-2 mabs. N42mab and N43mab recognize IgV domain of nectin4.

FIG. 8: Treatment of SUM190 grafted NSG mice with N41mab-MMAE induces a long-lasting tumor regression time period A: NSG mice were orthotopically xenografted bilaterally with the SUM190 cells embedded in Matrigel. This breast tumor cell line expresses equal amount of HER2 and nectin4 at cell surface. Three different ADC were tested: N41mab-vcMMAE, Ha22-2-vcMMAE and T-DM1.

Treatment of mice starts when tumors reach 200 mm$^3$ (100%). At this time period, two doses of ADCmabs (2.5 and 10 mg/kg) were administrated i.v. twice at day 0 and day 4 post-graft. All three ADC were active and reduced tumor development. N41mab-MMAE induced the longest lasting period of regression at 2.5 and 10 mg/kg respectively. B: Percentage weight variation measurements according to respective treatments (10 mg/kg). No adverse effects were noted during the experiment. C: Median time for tumors to reach 200 mm$^3$ after initial treatment.

Figure 9:
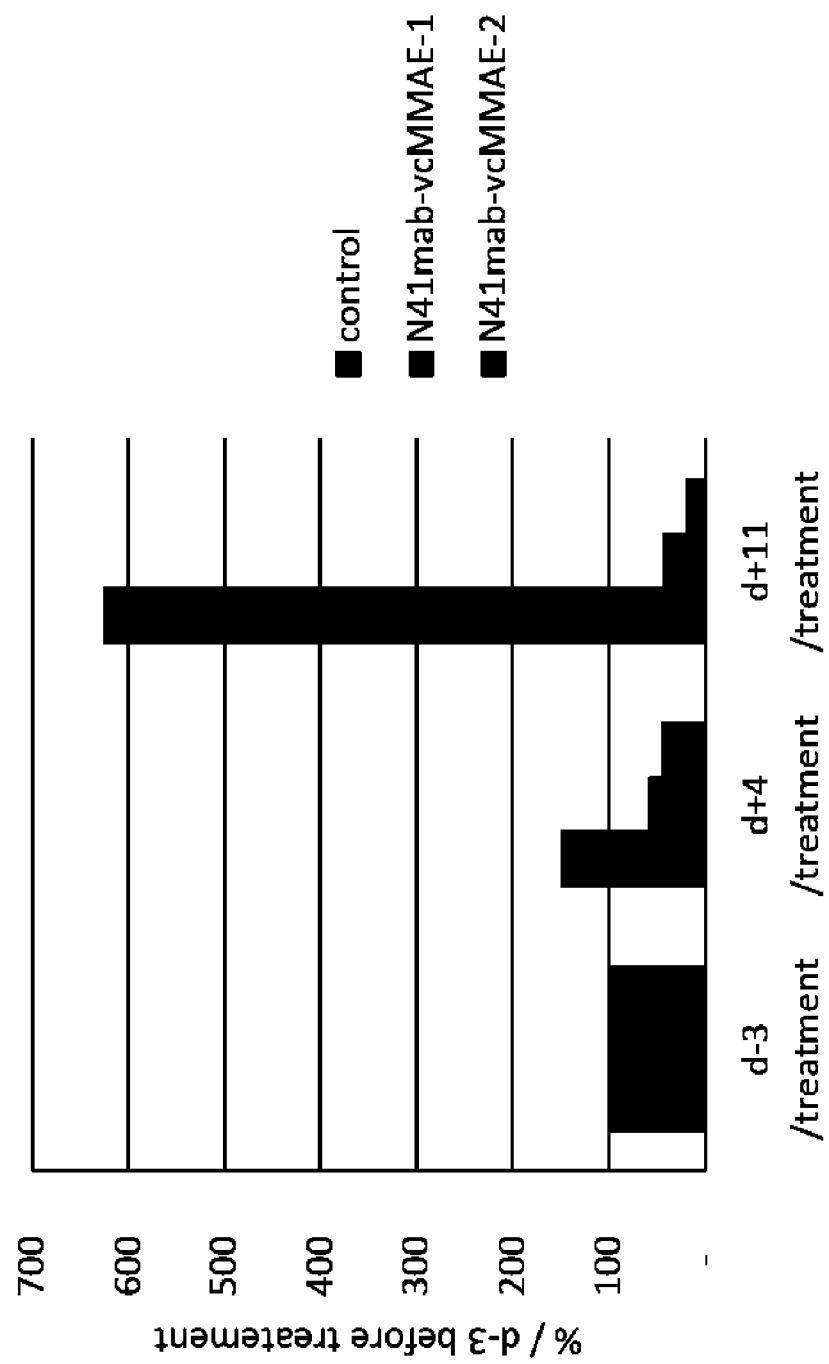

FIG. 9: Treatment of metastatic NSG mice with N41mab-MMAE

Metastatic NSG mice were obtained by i.v. injection of luciferase expressing SUM190 cells. Mice developed metastases at different sites. Quantification of luminescence using PhotonIMAGER (column 1=control; column 2=N41mab-vcMMAE-1; column 3=N41mab-vcMMAE-2).

Together, these data point to a marked anti-tumor activity of N4mab1-vcMMAE both in primary and metastatic lesions.

EXAMPLES

Example 1

Material & Methods

Cell Lines:

Human breast carcinoma cell line MDA-MB-231 (ATCC, Manassas, Va.) was cultured at 5% CO2 in DMEM supplemented with 10% FBS (fetal bovine serum), 50 IU/ml penicillin, 50 µg/ml streptomycin, and 2 mM glutamine. The cells were transfected with expression vector p3XFLR4.C1 containing a PVRL4 cDNA [x]. SUM-185, SUM-190 and SUM-225 breast carcinoma lines were kindly provided by Dr S. P. Ethier (University of Michigan). They were cultured in Ham's F12 medium with 5% FBS, non-essential amino acids, 10 µg/ml insulin, 1 µg/ml hydrocortisone, 50 IU/ml penicillin, 50 µg/ml streptomycin and 2 mM glutamine. BT-474 (ERBB2+) breast carcinoma cell line (ATCC) was cultured in RPMI supplemented with 10% FBS, 10 µg/ml insulin, 50 IU/ml penicillin, 50 µg/ml streptomycin, and 2 mM glutamine.

ELISA:

A sandwich enzyme-linked immunosorbent assay was used to control specificity of N41mab antibody and to perform competition assays between mabs. Ninety-six-well trays were coated with 5 µg/ml of nectin4V-Fc or nectin1V-Fc (comprising only the IgV domain) overnight at +4° C. After washes and saturation with PBS 1% BSA cells were incubated overnight with 0.625 µg/ml of N41mab. Peroxydase conjugated goat anti mouse antibody was incubated 2 h at 25° C. (Pierce). In the case of competition, binding of peroxidase conjugated N41mab was measured in the presence of vairable concentration of "cold" mab. One hundred ul of peroxidase substrate was added (One Step ABST, Pierce), and OD was read at 405 nm.

Flow Cytometry:

FACS analysis of MDAMB231 cell line transfected with the N-terminal Flag-Tagged epitope of Nectin4 using 2 µg/ml N41mab antibody. Cells were then stained with phycoerythrin conjugate goat anti mouse antibody (Beckman-Coulter).

Immunoblot Analysis:

Immunoblot experiments: analysis of cell lysate MDAMB231 nectin4 cells. Cells in 100-mm dishes were washed 3 times with ice-cold PBS and then resuspended for 30 min in 750_1 of ice cold lysis buffer containing 50 mM Hepes, pH 7.5, 150 mM NaCl, 1.5 mM MgCl2, 1 mM EGTA, 1% Triton X-100, and 10% glycerol. A protease inhibitor mixture was added as recommended by the manufacturer (Roche Diagnostics). Lysates were heated in SDS sample buffer (60 mM Tris-HCl, pH 6.7, 3% SDS, 2% (v/v) 2-mercaptoethanol, and 5% glycerol), separated by 8% SDS-PAGE, semidry-transferred to polyvinylidene difluoride membranes (Immobilon-P, Millipore, Boston, Mass.), probed with 1 µg/ml MOPC21, anti-FLAG M2, and N41mab, using the Mini-Protean II multiscreen apparatus. Visualization was done with ECL (Pierce).

Production of Antibody Drug Conjugate (ADC):

Briefly, conjugate has been produced from purified N41mab and Ha22-2 monoclonal antibody. The linker used is the MC-Val-Cit-PAB-PNP (Maleimidocaproyl-L-valine-L-citrulline-p-aminobenzyl alcohol p-nitrophenyl carbonate) covalently conjugated to monomethyl auristatin-E (MMAE). Drug to antibody ratio was 4.73 and 4.04 respectively.

Cell Growth/Viability Measurement:

To analyze the effect of ADC, cell growth was measured using the alamarBlue staining procedure as recommended by the manufacturer (Biosource, CA, USA). The test incorporates a fluorescent oxidation-reduction indicator. Fluorescence intensity is proportional to cellular metabolic reduction. Experiments were done by incubating 3000 cells/well in triplicate with serial dilutions of ADC at Day 0 in 96 well plates. AlamarBlue was measured at Day 5 by incubating 1/10 volume of alamarBlue solution for 2 h at 37° C. and read at 595 nm (FLUOstar Optima, BMG Labtech).

Invasion Assay:

The invasion assay was performed using the 24 cell culture inserts with 8 mm pore size membrane coated with Matrigel (BD BioCoat Growth Factor reduced Matrigel Invasion Chamber (Becton Dickinson, MA, USA)). Chemoattractant (10% FCS) was added to the wells and $10^5$ cells were loaded in the insert in RPMI 0.1% BSA. Plates were incubated for 72 h at 37° C. After migration, nonmigratory cells on the upper membrane surface were removed with cotton tipped swabs (four times per insert) and the migratory cells attached to the bottom surface of the membrane were stained for 20 min with 0.2% crystal violet in ethanol (Sigma). After five washes with 200 ml distilled water, invasive cells were counted with an inverted microscope. Each determination represents the average of three individual experiments done in duplicate.

Mouse Experiments:

NOD/SCID (nonobese diabetic/severe combined immunodeficient)/gc null mice (NSG) were obtained from Charles River Laboratory (Margate, UK).

Luciferase-expressing cells were transplanted in mice, either subcutaneously or in caudal vein or in mammary fat pads (7-week-old female). Treatment with N41mab or ADC was performed as mentioned in the respective experiments. Bioluminescence analysis was performed using PhotonIMAGER (BiospaceLab), following intraperitoneal injection of luciferin (30 mg/kg). Tumor volume was calculated using the formula V ¼ 0:52 (L×W2). After completion of the analysis, autopsy of mice was done and organ luminescence was assessed.

Results

The results are depicted in FIGS. 1-9.

Example 2

Material & Methods

Patients and Breast Cancer Samples. Ethics Statement.

The clinical samples had been profiled using DNA microarrays for gene expression analyses. Our own data set included 353 cases representing pretreatment invasive carcinomas from patients non-metastatic at diagnosis. The study was approved by our institutional review board (the Institut Paoli Calmettes (IPC) "Comité d'Orientation Stratégique" agreement n° 15-002). Each patient gave a written informed consent for research use. We pooled our series with 17 available data sets comprising at least one probe set representing PVRL4. These sets were collected from the National Center for Biotechnology Information (NCBI)/ Genbank GEO and ArrayExpress databases, and authors' website (data not shown). The final pooled data set included 5,673 non-redundant, non-metastatic, non-inflammatory, primary, invasive breast cancers with PVRL4 mRNA expression and clinicopathological data available (data not shown). For protein expression, an analysis of a consecutive panel of 61 TNBC samples at the time of diagnosis and prior to systemic therapy was obtained from women treated at our Institute. Informed consent for study enrollment was obtained for each patient and the study was approved by our institutional review board (data not shown).

Gene Expression Data Analysis

Our own gene expression data set had been generated using Affymetrix U133 Plus 2.0 human microarrays (Affymetrix®, Santa Clara, Calif., USA) as previously described (21). MIAME-compliant data are deposited in the GEO database (GSE31448). PVRL4 expression was measured by analyzing different probe sets whose identity and specificity were verified using the NCBI program BLASTN 2.2.31+ (data not shown). Data analysis required pre-analytic processing. First, each data set was normalized separately, using quantile normalization for the available processed non-Affymetrix data (Agilent, SweGene, Illumina), and Robust Multichip Average (RMA) (22) with the nonparametric quantile algorithm for the raw Affymetrix data. Normalization was done in R using Bioconductor and associated packages. In the second step, hybridization probes were mapped across the different technological platforms represented, using their EntrezGeneID. When multiple probes mapped to the same GeneID, we retained the one with the highest variance in a particular dataset. To avoid biases related to immunohistochemistry analyses across different data sets and thanks to the bimodal distribution of corresponding mRNA expression levels, estrogen receptor (ER), progesterone receptor (PR), and HER2 expression (negative/positive) was defined at the transcriptional level using mRNA expression data of ESR1, PGR, and ERBB2 respectively (23). Different multigene classifiers were then applied to each data set separately. The intrinsic molecular subtypes of tumors were defined using the mRNA expression levels of ESR1, PGR, and ERBB2 (HR+ for ESR1+ and/or PGR+ and; ERBB2− tumors; ERBB2+ for ERBB2+ tumors, and TN for ESR1−, PGR− and; ERBB2− tumors) and using the PAM50 classifier (24). Because of the presence of PVRL4 in the basal gene cluster, we also analyzed three prognostic gene expression signatures (GES) linked to immune response and validated in ER-, TN or basal breast cancers: the "immune response GES" (25), the "LCK GES" (26), and the "kinase immune GES" (27). Before analysis of PVRL4 mRNA expression, expression data were standardized within each data set using the luminal A population as reference, allowing us to exclude biases due to laboratory-specific variations and to population heterogeneity and to make all data sets comparable. As previously reported (28), principal component analysis (PCA) applied to all tumors and the PAM50 genes prior and after the standardization allowed to verify the accuracy of the normalization.

Anti-Nectin-4 Monoclonal Antibodies Production and Selection

Six different monoclonal antibodies directed against the distal IgV-like domain of nectin-4 (mab1 to mab6) were produced and analyzed. Recombinant soluble chimeric nectin4 V-Fc protein was used to immunize mice (6). Screening of hybridoma derived antibody against nectin-4 was done by flow cytometry using transfected MDA-MB-231 cells and ELISA.

Immunohistochemistry (IHC)

IHC was carried on 5 μm sections from frozen tissue. Sections were fixed in acetone for 10 min, air-dried for 10 min and rehydrated in TBST. Staining was done with 0.5 μg/ml mab1/N41mab for 3 h at 37° C. Secondary antibody OmnipMap anti-Ms HRP (Multimer HRP, Roche) was incubated for 15 min. Counterstaining was then done with Hematoxylin II and bluing reagent (Roche). Results were scored (Quick score) by multiplying the percentage of positive cells (P) by the intensity (I). Formula: $QS=P \times I$. Maximum score is 300.

Cell Lines

Human breast carcinoma cell line MDA-MB-231 (ATCC, Manassas, Va.) was cultured at 5% CO2 in DMEM supplemented with 10% FBS (fetal bovine serum), 50 IU/ml penicillin, 50 μg/ml streptomycin, and 2 mM glutamine. The cells were transfected with expression vector p3XFLR4.C1 containing a PVRL4 cDNA(7). SUM190 breast carcinoma line was kindly provided by Dr S. P. Ethier (University of Michigan) and was cultured in Ham's F12 medium with 5% FBS, non-essential amino acids, 10 μg/ml insulin, 1 μg/ml hydrocortisone, 50 IU/ml penicillin, 50 μg/ml streptomycin and 2 mM glutamine.

Production of ADC

ADC production was performed by Concortis (San Diego, Calif., USA). Conjugates were produced from purified mab1/N41mab monoclonal antibody. The linker used was the MC-Val-Cit-PAB-PNP (Maleimidocaproyl-L-valine-L-citrulline-paminobenzyl alcohol p-nitrophenyl carbonate) covalently conjugated to monomethyl auristatin-E (MMAE). This cleavable linker was selected as it induced potent bystander killing. The drug to antibody ratio was 4.73.

ELISA

A sandwich enzyme-linked immunosorbent assay was used to control the specificity of the N41mab antibody. Ninety-six-well trays were coated with 5 μg/ml of nectin4V-Fc or nectin1V-Fc (comprising only the IgV domain) overnight at +4° C. After washes and saturation with PBS 1% BSA cells were incubated overnight with 0.625 μg/ml of mab1/N41mab. Peroxydase-conjugated goat anti-mouse antibody was incubated 2 h at 25° C. (Pierce). One hundred μl of peroxidase substrate was added (One Step ABST, Pierce), and OD was read at 405 nm.

Flow Cytometry

FACS analysis of MDA-MB-231 cells transfected with the N-terminal Flag-Tagged epitope of Nectin4 was done using 2 □g/ml mab1/N41mab antibody. Cells were then stained with phycoerythrin-conjugated goat anti mouse antibody (Beckman-Coulter).

Immunoblot Analysis

Nectin-4 expression was analyzed in MDA-MB-231 nectin-4 cells in 100-mm dishes, washed 3 times with ice-cold PBS and then resuspended for 30 min in 750 μl of ice cold lysis buffer containing 50 mM Hepes, pH 7.5, 150 mM NaCl, 1.5 mM MgCl2, 1 mM EGTA, 1% Triton X-100, and 10% glycerol. A protease inhibitor mixture was added as recommended (Roche Diagnostics). Lysates were heated in SDS sample buffer (60 mM Tris-HCl, pH 6.7, 3% SDS, 2% (v/v) 2-mercaptoethanol, and 5% glycerol), separated by 8% SDS-PAGE, semidry-transferred to polyvinylidene difluoride membranes (Immobilon-P, Millipore, Boston, Mass., USA), probed with 1 μg/ml MOPC21, anti-FLAG M2, and mab1/N41mab, using the Mini-Protean II multiscreen apparatus. Visualization was done with ECL (Pierce).

Cell Growth/Viability Measurement

To analyze the effect of ADC, cell growth was measured using the alamarBlue staining procedure as recommended by the manufacturer (Biosource, CA, USA). The test incorporates a fluorescent oxidation-reduction indicator. Fluorescence intensity is proportional to cellular metabolic reduction. Experiments were done by incubating 3000 cells/well in triplicate with serial dilutions of ADC at Day 0 in 96-well plates. AlamarBlue was measured at day 5 by incubating 1/10 volume of alamarBlue solution for 2 h at 37° C. and read at 595 nm (FLUOstar Optima, BMG Labtech).

Animal Models

All experiments were performed in agreement with the French Guidelines for animal handling and approved by local ethics committee (Agreement n° 01152-01). NOD/SCID/γc null mice (NSG) were obtained from Dr. C. Rivers (Margate, UK). Mice were housed under sterile conditions with sterilized food and water provided ad libitum and maintained on a 12-h light and 12-h dark cycle. SUM190 cells were inoculated in the mammary fat pad with (0.5× 106) suspended in 50% phenol red-free Matrigel (Becton Dickinson Bioscience). The patient derived tumor cells (PDX models) were inoculated in the mammary fat pad with (0.2 to 0.5×106) suspended in 50% phenol red-free Matrigel.

Tumor growth was monitored by measuring with a digital caliper and calculating tumor volume (length×width2×π/6). All animals were randomly assigned into treatment groups, such that the mean tumor volume for each group was 100 to 200 mm3. Treatment with ADC was performed as mentioned in the respective experiments. Luciferase-expressing SUM190 cells (0.5×106 cells in 100 μL of PBS) were inoculated in the tail vein of NSG mice. Bioluminescence analysis was performed using PhotonIMAGER (Biospace Lab) following addition of endotoxin-free luciferin (30 mg/kg). After completion of the analysis, autopsy of mice was performed, and organ luminescence was assessed. Among a collection of PDX developed in NSG mice and previously characterized at CRCM (16), we selected 9 basal-like PDX models (obtained from primary TNBCs) for IHC studies. Four PDX were treated with ADC as mentioned in the respective experiments.

Statistical Methods

Correlations between tumor groups and clinicopathological features were analyzed using the Fisher's exact test. Metastasis-free survival (MFS) was calculated from the date of diagnosis until the date of distant relapse. Follow-up was measured from the date of diagnosis to the date of last news for event-free patients. Survivals were calculated using the Kaplan-Meier method and curves were compared with the log-rank test. Univariate and multivariate survival analyses were done using Cox regression analysis (Wald test). Variables tested in univariate analyses included patients' age at time of diagnosis (≤50 years vs >50), pathological type (ductal vs noductal), pathological tumor size (pT: pT1 vs pT2-3), pathological axillary lymph node status (pN: negative vs positive), pathological grade (1-2 vs 3), and PVRL4 expression ("high" vs "low"). Variables with a p-value <0.05 in univariate analysis were tested in multivariate analysis. All statistical tests were two-sided at the 5% level of significance. Statistical analysis was done using the survival package (version 2.30) in the R software (version 2.9.1; http://www.cran.r-project.org/). We followed the reporting REcommendations for tumor MARKer prognostic studies (REMARK criteria). Data are presented as mean+s.e.m. and were calculated by Mann-Whitney test using GraphPad Prism software. P<0.05 was considered statistically significant. Data are representative of at least three experiments.

Results:

Nectin4/PVRL4 is a TNBC Specific Biomarker

We examined PVRL4 mRNA expression in a pooled series of 5673 invasive breast cancers profiled using DNA microarrays and five different PVRL4 probes 100% specific (see materials and methods). Whole-genome clustering of our own 353-sample series showed that PVRL4 was in the "basal" gene cluster (data not shown). High PVRL4 expression was associated with poor-prognosis features, including both triple negative (TN) subtype and the PAM50 basal subtype (data not shown). Metastasis-free survival (MFS) data were available for 1,037 patients, including 613 without metastatic relapse (median follow-up, 83 months) and 424 with metastatic relapse (median time to relapse, 24 months). The 5-year MFS rate was 61% (95CI, 0.58-0.65). In the whole population, high PVRL4 expression was associated with shorter MFS (p=0.0143, log-rank test), (data not shown). High PVRL4 expression was actually associated with MFS in the TN subgroup only, with 5-year MFS of 47% (95CI, 0.40-0.55) versus 62% (95CI, 0.51-0.74) in the "PVRL4-high" and "PVRL4-low" groups, respectively (p=0.014, log-rank test), (FIG. 1c) and PVRL4 expression retained prognostic impact (p=0.036, Wald test; HR=1.53 [1.02-2.30]) in multivariate analysis (Table 1). We next examined expression of nectin-4 at the protein level by immunohistochemistry in 61 TNBCs, 12 of them previously profiled using DNA microarrays. The monoclonal antibody used for this analysis, selected from our screening (see next paragraph), recognized the distal IgV-like domain of human nectin-4 and did not cross-react with the other human nectins or with mouse nectin-4 (data not shown). Based on the QuickScore (QS) semi-quantitative assessment, we distinguished a "nectin-4-high group" with a QS>100 and a "nectin-4-low group" with a QS<100 representing 62% and 38% of TNBCs, respectively (data not shown). Nectin-4 expression was detected at the plasma membrane. mRNA and protein expression of nectin-4 showed good correlation (data not shown; p=0.0022). Importantly, nectin-4 was detected neither in the normal mammary gland epithelium (data not shown) nor in 30 different adult normal tissues except the skin (data not shown). These results established nectin-4 as both a new cell surface biomarker and a potential target for TNBCs.

ADC-Based Targeting of Nectin-4 In Vitro

We produced and tested six monoclonal antibodies (mAbs) directed against the IgV-like distal domain of nectin-4 to isolate a mAb able to induce internalization. MAbs were evaluated for EC50, maximum binding capacity, cell surface internalization and cytotoxicity (data not shown). Internalization was tested using Flag-tagged nectin-4 expressed in MDA-MB-231 cells and FITC-labelled anti-Flag antibody (M2, Sigma-Aldrich) to quantify residual surface nectin-4. Mab1 was the most efficient antibody. It induced a 60% decrease of cell surface nectin-4 in 24 h and a 60% cell growth inhibition after incubation with a goat anti-mouse monoclonal antibody conjugated to saporin (mab-ZAP kit, ATS-bio). Internalization and cytotoxicity were correlated (R2=0.9606). Mab1 did not affect cell viability in vitro and tumor cell growth in vivo (data not shown). Mab1 was then conjugated to monomethyl auristatin-E (MMAE) via a cleavable valine-citrulline (vc) dipeptide linker (thereafter called N41mab-vcMMAE, ADC) to produce an ADC, which was tested in vitro for specificity and efficacy on selected breast cancer cell lines. MDA-MB-231 cells, which express nectin-1, nectin-2, and nectin-3 but not nectin-4, were not sensitive to the ADC. However, ectopic expression of nectin-4 conferred sensitivity with an IC50=2 ng/ml (data not shown). SUM190 cells, which express endogenous nectin-4, were sensitive with an IC50=4 ng/ml (data not shown). These data showed the specificity and the efficacy of N41mab-vcMMAE.

ADC-Based Targeting of Nectin-4 In Vivo

Activity of our ADC was tested in three in vivo models of TNBC developed in immunocompromised NSG mice. First, mice xenografted with SUM190 cells were treated with two successive i.v. doses of N41mab-vcMMAE (data not shown). These doses were not toxic for mice (data not shown). N41mab-vcMMAE induced a rapid (4 days) and dose-dependent tumor regression that lasted up to 40 days (data not shown). After relapse, tumors still kept their sensitivity to the ADC, at least over a period of 6 months (data not shown).

Second, we used patient-derived xenografts (PDX) of primary TNBC. These pre-clinical models recapitulate breast cancer physiopathology (16). Localization and levels of nectin-4 expression in PDX were similar to that found in TNBC patients (data not shown). Nectin-4 expression was prominently found at the plasma membrane in 7/9 PDX (QS>100). TNBC PDX mice with different QS were treated with two successive i.v. doses of ADC. Clinical response was roughly correlated with the level of expression: a rapid and marked tumor burden regression (up to 35 days) was observed for PDX400 (QS=300), PDX 317 (QS=140), to a lesser extent for PDX348 (QS=100) (data not shown) but not for PDX434 (QS=10) data not shown). In contrast, treatment of PDX 348 by docetaxel (3 times 10 mg/kg i.p.) was ineffective (data not shown).

Third, to evaluate ADC treatment efficacy in advanced disease, we treated PDX317 and PDX400 mice developing spontaneous metastatic lesions from primary tumors. Treatment of the two PDX with two successive i.v. doses of ADC, led to a rapid reduction and disappearance of all metastatic lesions observed by luminescence analysis over 35 days (data not shown). Metastasis recurrences were detected at day 28 and 43 post-ADC treatment for PDX400, and still not observed for PDX317 after 112 days. These results showed that N4mab1-vcMMAE had a marked anti-tumor activity both in nectin-4 expressing primary and metastatic TNBCs.

REFERENCES

Throughout this application, various references describe the state of the art to which this invention pertains. The disclosures of these references are hereby incorporated by reference into the present disclosure.

The invention claimed is:

1. An antibody having specificity to nectin-4 and having a heavy chain comprising i) the H-CDR1 of N41mab, ii) the H-CDR2 of N41mab and iii) the H-CDR3 of N41mab and
a light chain comprising i) the L-CDR1 of N41mab, ii) the L-CDR2 of N41mab and iii) the L-CDR3 of N41mab
wherein
the H-CDR1 of N41mab is defined by the sequence ranging from the amino acid residue at position 31 to the amino acid residue at position 35 in SEQ ID NO:1,
the H-CDR2 of N41mab is defined by the sequence ranging from the amino acid residue at position 50 to the amino acid residue at position 65 in SEQ ID NO:1,
the H-CDR3 of N41mab is defined by the sequence ranging from the amino acid residue at position 98 to the amino acid residue at position 105 in SEQ ID NO:1,
the L-CDR1 of N41mab is defined by the sequence ranging from the amino acid residue at position 24 to the amino acid residue at position 34 in SEQ ID NO:2,
the L-CDR2 of N41mab is defined by the sequence ranging from the amino acid residue at position 50 to the amino acid residue at position 56 in SEQ ID NO:2, and
the L-CDR3 of N41mab is defined by the sequence ranging from the amino acid residue at position 89 to the amino acid residue at position 96 in SEQ ID NO:2.

2. The antibody of claim 1 having a heavy chain identical to SEQ ID NO: 1 and a light chain identical to SEQ ID NO:2.

3. The antibody of claim 1 which is a chimeric antibody.

4. The antibody of claim 1 which is a humanized antibody which comprises the CDRs of the N41mab antibody.

5. A nucleic acid molecule encoding the antibody of claim 1.

6. The antibody of claim 1 which is conjugated to a cytotoxic moiety.

7. The antibody of claim 6 which is conjugated to a cytotoxic moiety selected from the group consisting of taxol; cytochalasin B; gramicidin D; ethidium bromide; emetine; mitomycin; etoposide; tenoposide; vincristine; vinblastine; colchicin; doxorubicin; daunorubicin; dihydroxy anthracin dione; a tubulin-inhibitor; Mertansine or a peptide analog, derivative or prodrug thereof; an antimitotic agent; dolastatin 10 or 15 or an analogue thereof; irinotecan or an analogue thereof; mitoxantrone; mithramycin; actinomycin D; 1-dehydrotestosterone; a glucocorticoid; procaine; tetracaine; lidocaine; propranolol; puromycin; calicheamicin or an analog or derivative thereof; an antimetabolite; an alkylating agent; a platinum derivative; duocarmycin A, duocarmycin SA, rachelmycin (CC-1065), or an analog or derivative thereof; an antibiotic; pyrrolo[2,1-c][1,4]-benzodiazepines (PDB); diphtheria toxin or derivative thereof, ricin toxin or derivative thereof, cholera toxin, Shiga toxin or a Shiga like toxin, pertussis toxin, tetanus toxin, soybean Bowman-Birk protease inhibitor, *Pseudomonas* exotoxin, alorin, saporin, modeccin, gelanin, abrin A chain, modeccin A chain, alpha-sarcin, *Aleurites fordii* proteins, dianthin proteins, a *Phytolacca americana* protein, *Momordica charantia* inhibitor, curcin, crotin, *Sapaonaria officinalis* inhibitor, gelonin, mitogellin, restrictocin, phenomycin, enomycin toxins; ribonuclease (RNase); DNase I, Staphylococcal enterotoxin A; pokeweed antiviral protein; and *Pseudomonas* endotoxin.

8. The antibody of claim 6 which is conjugated to an auristatin or a peptide analog, derivative or prodrug thereof.

9. A method of treating cancer in a subject in need thereof comprising administering to the subject a therapeutically effective amount of the antibody of claim 1.

10. The method of claim 9 wherein the cancer is a breast cancer, an ovarian cancer or a lung cancer.

11. The method of claim 9 wherein the cancer is a metastatic cancer.

12. A pharmaceutical composition comprising the antibody of claim 1.

13. A chimeric antigen receptor which comprises at least one VH and/or VL sequence of the antibody of claim 1.

14. The antibody of claim 7, wherein
a. the tubulin-inhibitor is maytansine or an analog or derivative thereof;
b. the antimitotic agent is monomethyl auristatin E or F or an analog or derivative thereof;
c. the antimetabolite is methotrexate, 6 mercaptopurine, 6 thioguanine, cytarabine, fludarabin, 5 fluorouracil, decarbazine, hydroxyurea, asparaginase, gemcitabine, or cladribine;
d. the alkylating agent is mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine or mitomycin C;
e. the platinum derivative is cisplatin or carboplatin;
f. the antibiotic is dactinomycin, bleomycin, daunorubicin, doxorubicin, idarubicin, mithramycin, mitomycin, mitoxantrone, plicamycin or anthramycin (AMC);
g. the diphtheria toxin or derivative thereof is diphtheria A chain, an active fragment of diphtheria toxin or a hybrid molecule of diphtheria toxin or diphtheria A chain;
h. the ricin toxin or derivative thereof is ricin A or a deglycosylated ricin A chain toxin;
i. the Shiga-like toxin is SLT I, SLT II, SLT IIV, LT toxin or C3 toxin; and/or
j. the *Phytolacca americana* protein is PAPI, PAPII or PAP-S.

* * * * *